(12) United States Patent
Sekine et al.

(10) Patent No.: US 7,863,455 B2
(45) Date of Patent: Jan. 4, 2011

(54) ELECTROCHEMICALLY ACTIVE LIGAND FOR SEQUENCE-SPECIFIC DETECTION OF DOUBLE-STRANDED NUCLEIC ACID MOLECULE

(75) Inventors: Mitsuo Sekine, Yokohama (JP); Kohji Seio, Yokohama (JP); Masahiro Mizuta, Yokohama (JP); Takeshi Terada, Yokohama (JP)

(73) Assignee: Japan Science and Technology Agency, Kawaguchi-shi Saitama (JP)

( * ) Notice: Subject to any disclaimer, the term of this patent is extended or adjusted under 35 U.S.C. 154(b) by 754 days.

(21) Appl. No.: 10/590,232

(22) PCT Filed: Feb. 23, 2005

(86) PCT No.: PCT/JP2005/003440

§ 371 (c)(1),
(2), (4) Date: Apr. 13, 2007

(87) PCT Pub. No.: WO2005/087784

PCT Pub. Date: Sep. 22, 2005

(65) Prior Publication Data

US 2007/0172826 A1    Jul. 26, 2007

(30) Foreign Application Priority Data

Feb. 24, 2004   (JP) ............................. 2004-047605

(51) Int. Cl.
    *C07F 15/02*        (2006.01)
(52) U.S. Cl. ..................................... 548/101
(58) Field of Classification Search ............... 548/101
    See application file for complete search history.

(56) References Cited

U.S. PATENT DOCUMENTS

2002/0068294 A1   6/2002  Takenaka
2002/0117396 A1   8/2002  Pak et al.

FOREIGN PATENT DOCUMENTS

JP    2003-000300 A    1/2003
JP    2003-83968 A     3/2003
WO    WO-00/31750 A1   6/2000

OTHER PUBLICATIONS

Kohji Seio et al.; Synthesis and Properties of a Pyrrole-imidazole Polyamide Having a Ferrocene Dicarboxilic Amide Linker; Tetrahedron Letters, 2004, 45 (36); pp. 1-4.
Markus Scherer et al.; A bridged pyrrolic ansa-ferrocene. A new type of anion receptor, Chemical Communications, 1998, 1, pp. 85-86.
Jahyo Kang et al.; Preparation of bis [palladacycles[ and application to asymmetric aza-Claisen rearrangement of allylic imidates, Tetrahedron Letters, 2002, 43 (52), 9509-9512.
Chunhai Fan et al.; Electrochemical interrogation of conformational changes as a reagentless method for the sequence-specific detection of DNA; A. J. Proc. Natl. Acad. Sci., Aug. 5, 2003, vol. 100, No. 16, pp. 9134-9137.
Milan Mrksich; Hairpin Peptide Motif. A New Class of Oligopeptides for Sequence-Specific Recognition in the Minor Groove of Double-Helical DNA; J. Am. Chem. Soc., 1994, No. 116, pp. 7983-7988.
Victor C. Rucker et al.; Sequence Specific Fluorescence Detection of Double Strand DNA; J. Am. Chem. Soc., 2003, No. 125, pp. 1195-1202.
Yong-Dong Wang et al.; DNA crosslinking and biological activity of a hairpin polyamidechlorambucil conjugate; Nucleic Acids Research, vol. 31, No. 4, 2003.
Shane Foister et al.; Shape Selective Recognition of T-A Base Pairs by Hairpin Polyamides Containing N-Terminal 3-Methoxy (and 3-Chloro) Thiophene Residues; Bioorganic & Medicinal Chemistry, No. 11, 2003, pp. 4333-4340.

*Primary Examiner*—Joseph R Kosack
(74) *Attorney, Agent, or Firm*—Birch, Stewart, Kolasch & Birch, LLP.

(57) ABSTRACT

The purpose of the present invention is to provide a compound that specifically binds to the base sequence of a double-stranded nucleic acid molecule. The compound can reduce the electrochemical signal/noise ratio (S/N) in electrochemical detection, and as a result, the detection sensitivity (precision) will be greatly improved so as to enable the determination of an ultratrace amount of nucleic acid molecule. The present invention relates to a ferrocene compound represented by the following general formula (I):

$$A \underset{O}{\overset{R_2}{\underset{|}{N}}} \begin{matrix} V^1-V^2-V^3\text{-}\text{-}V^n-V^{n+1}\text{-}\text{-}W \\ X^1-X^2-X^3\text{-}\text{-}X^m-X^{m+1}\text{-}\text{-}Z \end{matrix} \qquad (I)$$

wherein "A" represents a divalent ferrocene-containing linker or ferrocene-1,1'-yl, $R_2$ represents a hydrogen atom or alkyl; "n" and "m" represent any natural numbers; and "V" and "X" represent the pyrrole-imidazole-polyamide (PIPA); to a ligand consisting of said ferrocene compound for sequence-specific detection of double-stranded nucleic acid molecules; to a method for electrochemical detection of double-stranded nucleic acid molecules 8 with the use of said ligand; and to an apparatus or device for the electrochemical detection with the use of said ligand.

12 Claims, 3 Drawing Sheets

US 7,863,455 B2

ELECTROCHEMICALLY ACTIVE LIGAND FOR SEQUENCE-SPECIFIC DETECTION OF DOUBLE-STRANDED NUCLEIC ACID MOLECULE

FIELD OF THE INVENTION

The invention relates to an electrochemically active ferrocene compound that may be used as a ligand for sequence-specific detection of a double-stranded nucleic acid molecule and the like.

BACKGROUND ART

"DNA microarray" or "DNA chip" is a collective term that means slide glass or silicon base having DNA sequence fragments aligned in a high density thereon, which is an analytical tool used for gene expression analysis that have been recently developed. Transcription amount of each gene may be detected by using as an index intensity of hybridization of a prepared RNA or DNA sample (target). Such DNA microarray has now been used for the detection of single nucleotide polymorphism (SNP) as well.

The typical DNA chips that are known to be commercially available are an "Affimetrix-type" one sold by Affimetrix (USA) and a "Stanford-type" one developed by Stanford University (USA). The Affimetrix-type chip is made by synthesis of a DNA probe on silicon base in a high density so that it can fix from several thousands to several tens of thousands of kinds of probes on one chip. On the other hand, the Stanford-type chip is made by dropping DNA fragments that have been prepared in advance on slide glass. The detection with those chips is usually carried out by image analysis with the use of fluorescent pigments bound to the target.

Recently, a technique has been developed in which the results of hybridization between the probe and target are detected electrochemically in stead of fluorescent pigment (electrochemical Array: ECA chip) (Drummond, T. G.; Hill, M. G.; Barton, J. K. Natl. Biotechnol. 203, 21, 1192-1199). Such electrochemical detection is preformed with the use of an intercalating agent that is electroconductive and having a property of being intercalated between neighboring base pairs of a double-stranded DNA. There are already known electroconductive intercalating agents such as anthraquinone, naphthquinone, polyphyne and ferrocene. An example of the detection of a gene using ferrocene derivatives was reported (Fan, C.; Plaxco, K. W.; Heeger, A. J. Proc. Natl. Acad. Sci. USA, 2003, 100, 9134-9137). Furthermore, a DNA chip with the use of ferrocenyl naphthalene diimide derivatives as the intercalating agent and various methods using said chip have been proposed (Japanese Patent Application Publications No. 2003-300 and No. 2003-83968).

On the other hand, hairpin-type pyrrole-imidazole-polyamide (PIPA) usually forming 6-mer or 8-mer is known as a prototype of synthetic organic molecules that can site-specifically recognize a DNA sequence, and its potentiality for gene regulation has been therefore proposed (Mrksich, M.; Parks, M. E.; Derevan, P. B. J. Am. Chem. Soc. 1994, 116, 7983-7988). Furthermore, many attempts have been reported in which the structure of PIPA was modified in order to alter their functions and properties. For example, some research groups have proposed modification of PIPA with a fluorescent pigment (Rucker, V. C.; Foister, S.; Melander, C.; Dervan, P. B. J. Am. Chem. Soc. 2003, 125, 1195-1202), oranalkylating agent (Wang, Y-D.; Dziegielewski, J.; Wurtz, N. R.; Dzielewska, B.; Dervan, P. B.; Beerman, T. A. Nucleic Acids Res. 2003, 31, 1208-1215, et al.), in order to use it as a tool for the detection of a gene and a potential anti-cancer agent.

In addition to the above functional modification, some other research groups tried the modification of the structure of PIPA into other heterocyclic compounds for the purpose of improvement of affinity and sequence-specificity of pyrrole and imidazole for the double-stranded DNA, and some of them reported success of the improvement of sequence-specificity (Foister, S.; Marques, M. A.; Doss, R. M.; Dervan, P. B. Bioorganic Med. Chem. Lett. 2003, 11, 4333-4340, et al.)

[Patent Document 1] Japanese Patent Application Publications No. 2003-300

[Patent Document 2] Japanese Patent Application Publications No. 2003-83968

[Non-Patent Document 1] Fan, C.; Plaxco, K. W.; Heeger, A. J. Proc. Natl. Acad. Sci. USA, 2003, 100, 9134-9137

[Non-Patent Document 2] Mrksich, M.; Parks, M. E.; Derevan, P. B. J. Am. Chem. Soc. 1994, 116, 7983-7988

[Non-Patent Document 3] Rucker, V. C.; Foister, S.; Melander, C.; Dervan, P. B. J. Am. Chem. Soc. 2003, 125, 1195-1202

[Non-Patent Document 4] Wang, Y-D.; Dziegielewski, J.; Wurtz, N. R.; Dzielewska, B.; Dervan, P. B.; Beerman, T. A. Nucleic Acids Res. 2003, 31, 1208-1215

[Non-Patent Document] Foister, S.; Marques, M. A.; Doss, R. M.; Dervan, P. B. Bioorganic Med. Chem. Lett. 2003, 11, 4333-4340

SUMMARY OF THE INVENTION

Problems to be Solved by the Invention

The intercalating agents that have been conventionally used for the electrochemical DNA chip have disadvantages that they may bind not only to the double-stranded DNA but also single-stranded DNA so as to generate other electrical signals than that based on the double-stranded DNA, or that a noise current generated by free intercalating agents will cause a detection noise, which will then increasing electrochemical signal/noise ratio (S/N).

It is well known that an authentic nucleotide may form a considerably stable mismatch base pair such as G-T, A-G and G-G pairs, which may generate false-positive signals in the above electrochemical detection methods using the conventional intercalating agents.

The present inventors have studied to develop a compound that can specifically recognize the base sequence of double-stranded nucleic acid molecule by means of modification of a linker region in the pyrrole-imidazole-polyamide structure. Finally they have succeeded in the synthesis of a compound having a ferrocene moiety in the linker region of the pyrrole-imidazole-polyamide structure, and overcome the above problems.

Means for Solving the Above Problems

Thus, the present invention relates as a first aspect to a ferrocene compound represented by the following general formula (I):

[Chemical Formula 1]

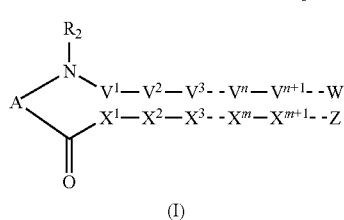

(I)

wherein "A" represents a divalent ferrocene-containing linker or ferrocene-1 μl'-yl, $R_2$ represents a hydrogen atom or alkyl; "n" and "m" represent any natural numbers; and "V" and "X" represent the following general formula (II) or (II-1):

[Chemical Formula 2]

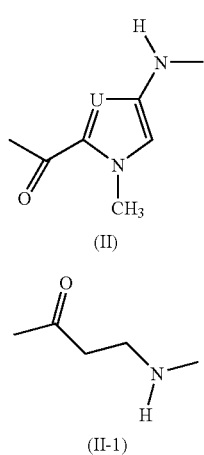

[Chemical Formula 3]

(II-1)

"W" represents the following general formula (III):

[Chemical Formula 4]

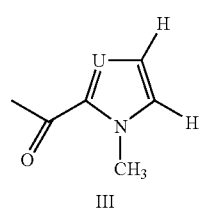

III wherein "U" in the general formulae (II) and (III) represents a nitrogen atom, methine or hydroxymethine; and "Z" represents the following general formulae (IV) or (V):

[Chemical Formula 5]

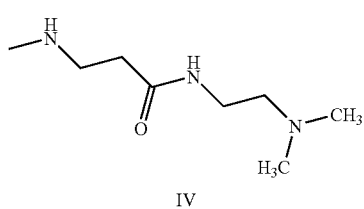

IV

-continued

[Chemical Formula 6]

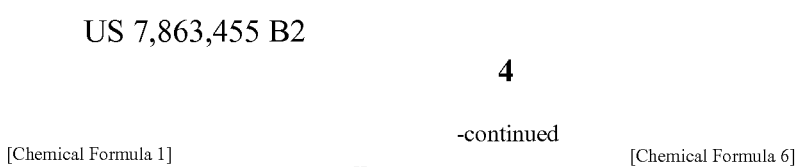

V and both ends of each of $V^n$ and $X^m$ in the general formula (I) form a (—CO—NH—) bond except that a bond on the side of the ferrocene-containing linker or ferrocene-1,1'-yl of V1 is (—CO—$NR_2$—).

The present compound represented by the general formula (I) consists of the divalent ferrocene-containing linker and two pyrrole-imidazole-polyamide (PIPA) regions bound to the linker.

The ferrocene-containing linker may therefore take any structure as long as it contains a ferrocene group and is compound (or atom group) showing the function mentioned above.

The numbers "n" and "m" are natural numbers, preferably in the range of 3-20, more preferably of 3-10. Furthermore, it is preferable that the number of "n" is smaller by one than that of "m" so that the total numbers of imidazole and pyrrole derivatives in the atom groups bound to the both sides of the ferrocene-containing linker will be finally the same to each other.

Preferable examples of the ferrocene-containing linker (A) include the compounds represented by following general formulae (VI), (VII) and (X):

[Chemical Formula 7]

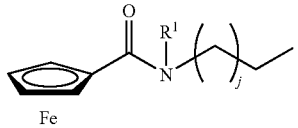

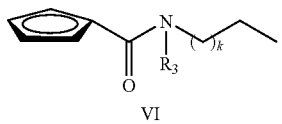

VI

[Chemical Formula 8]

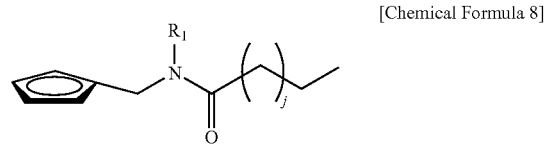

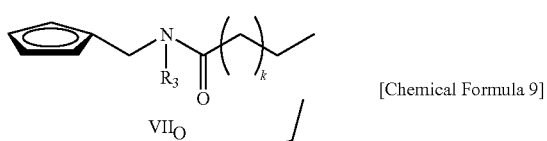

[Chemical Formula 9]

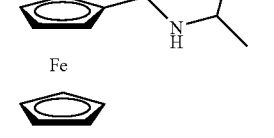

X wherein $R_1$ and $R_3$ represent a hydrogen atom or alkyl; "j" and "k" represent the same or different integer of from 0 to 5. $R_1$, $R_2$ and $R_3$ are preferably alkyl having one or several carbon atoms, such as a methyl group.
Specific examples of the above compounds include those represented by the formulae (VIII or 1a), (IX), (1b), (1c), (2) and (3):
[Chemical Formula 10]
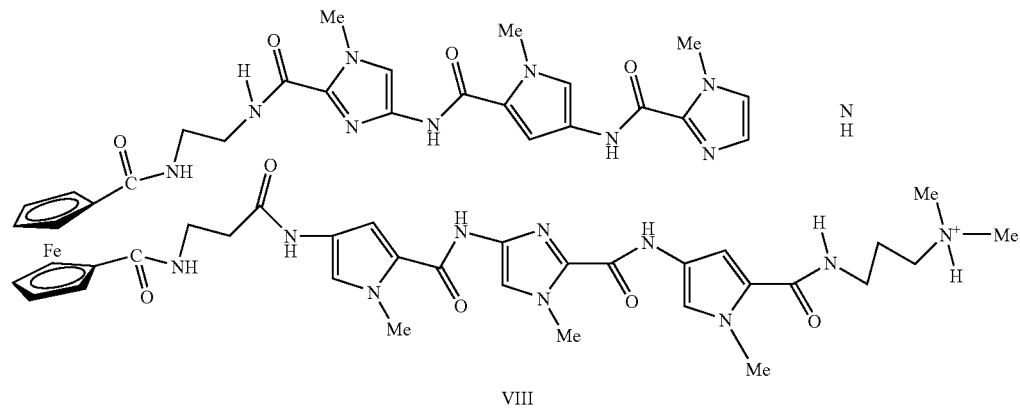
VIII
[Chemical Formula 11]
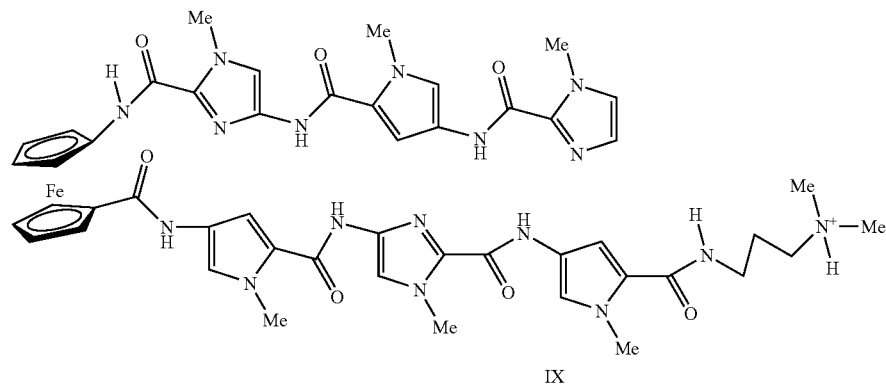
IX
[Chemical Formula 12]
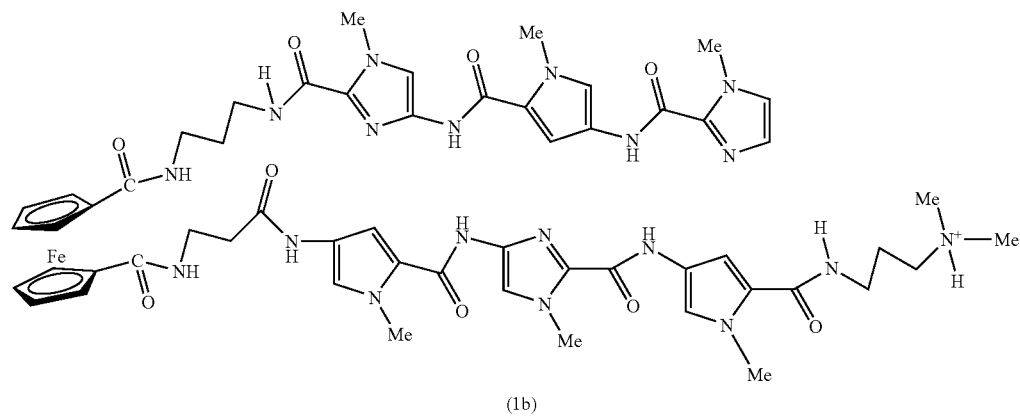
(1b)

-continued

[Chemical Formula 13]

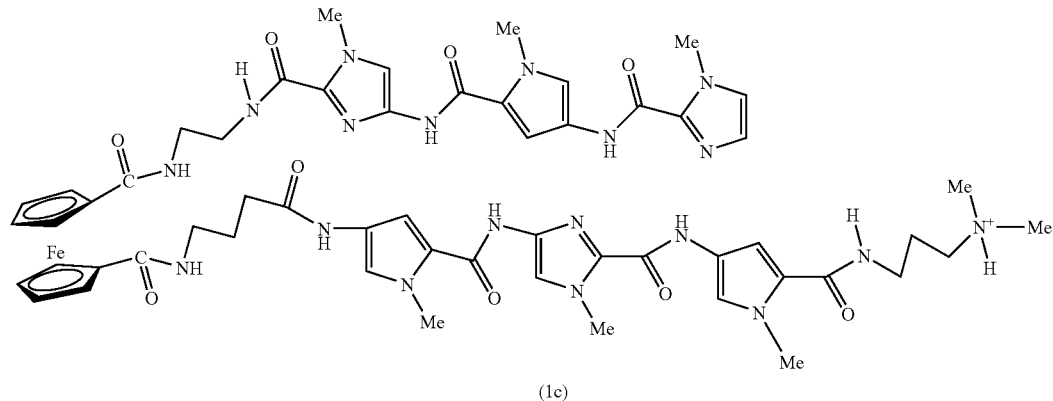

(1c)

[Chemical Formula 14]

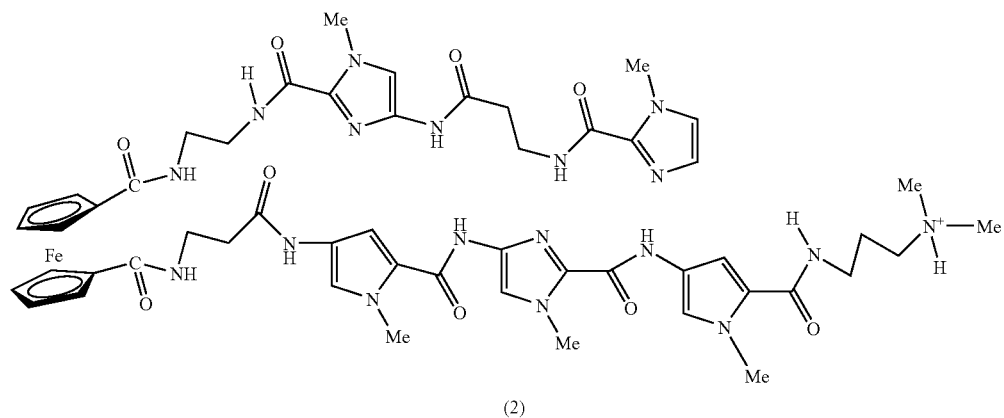

(2)

[Chemical Formula 15]

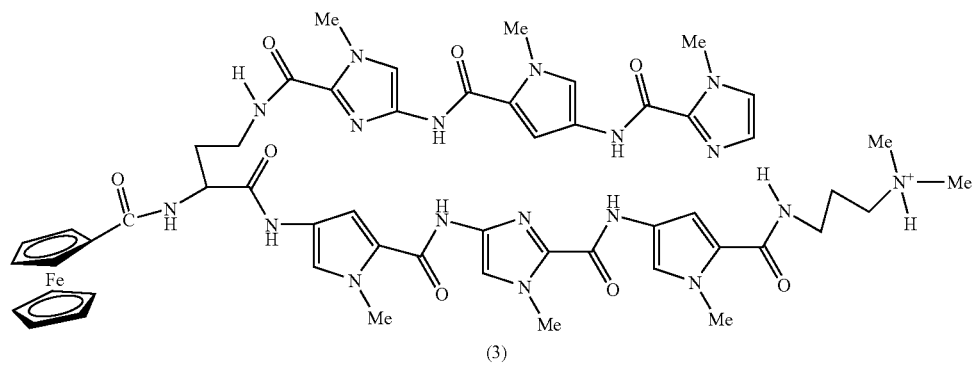

(3)

The compounds according to the present invention may be synthesized by the processes described in the following examples. Reaction conditions that are not specifically described in the present specification may be optionally and easily adopted by those skilled in the art.

Accordingly, the present invention relates as a second aspect to a method for the production of the ferrocene compound according to the present invention, comprising a condensation step with the use of ferrocene methyl dicarboxylate, aminoferrocene methyl carboxylate or ferrocene carboxylic acid as a staring material. The present method are exemplified in reaction schemes represented by Chemical Formulae 16 to 21, and include the methods comprising the steps described in the examples of the present specification.

The present invention relates as a third aspect to a ligand consisting of the ferrocene compound according to the present invention for sequence-specific detection of double-stranded nucleic acid molecules.

The present invention relates to as a forth aspect to a method for the electrochemical detection of double-stranded nucleic acid molecules and an apparatus or device for the electrochemical detection with the use of a compound that can sequence-specifically bind to the double-stranded nucleic acid molecules, such as the above ligand.

ADVANTAGES OF THE INVENTION

By using the compound that can sequence-specifically bind to the double-stranded nucleic acid molecules, such as the ferrocene compound represented by the general formula (I) it is possible to lower the electrochemical signal/noise ratio (S/N) in the electrochemical detection. As a result, Significant improvement of the detection sensitivity (precision) is attained, enabling a quantitative determination of an ultratrace amount of the double-stranded nucleic acid molecules.

BEST MODE FOR CARRYING OUT THE INVENTION

Figure 1:
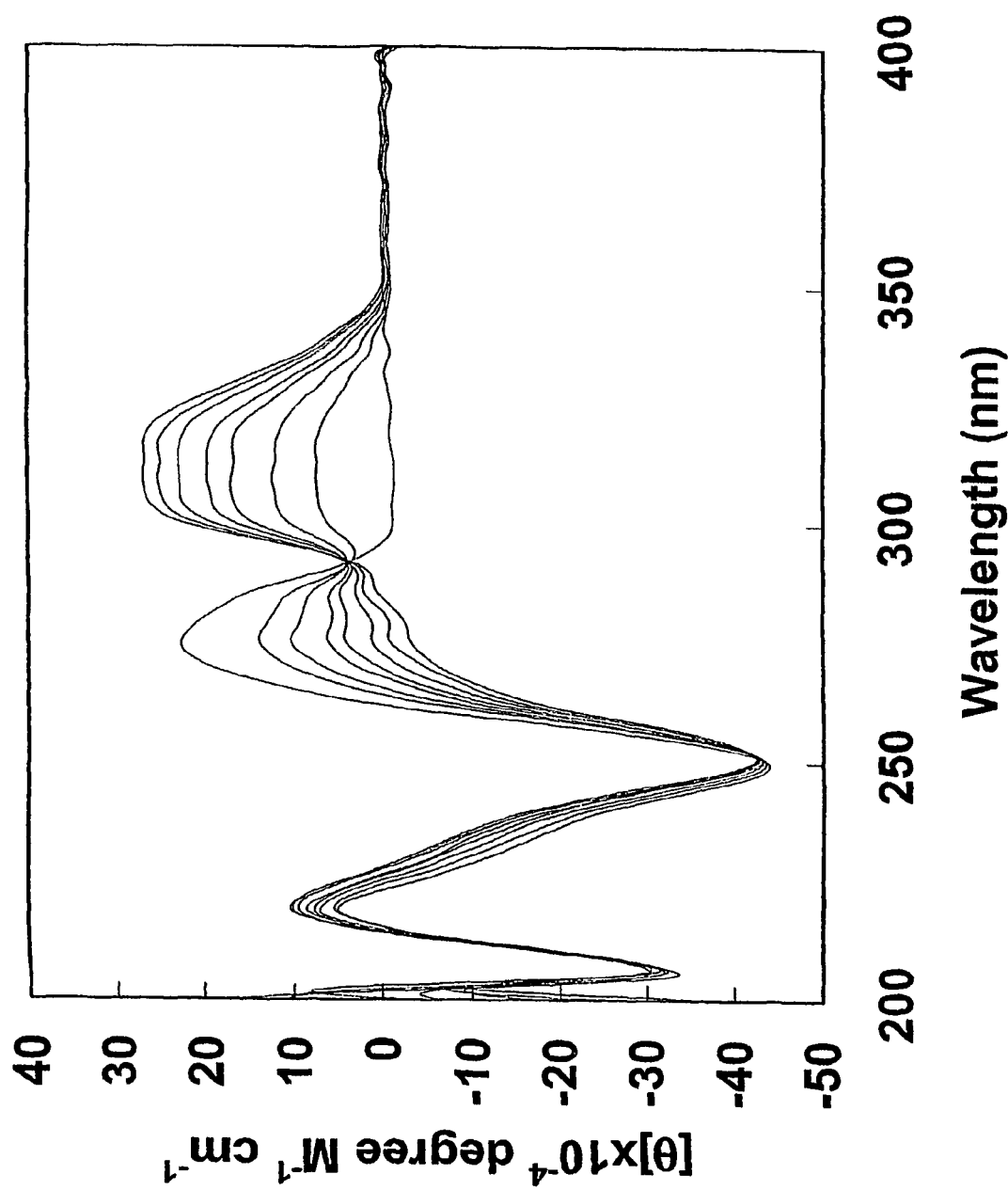
FIG. 1 shows CD profile in the titration of the 15-mer DNA prepared in Example 2. The reaction was carried out in 10 mM sodium cacodylate (pH 6.9) containing 10 mM KCl, 10 mM $MgCl_2$, 5 mM $CaCl_2$.

The term "nucleic acid" in the present specification means both DNA and RNA, and the double-stranded nucleic acid molecules include DNA-DNA and DNA-RNA and the like. For example, mRNA, cDNA that has been prepared by reverse transcription, and their fragment may be used as a sample (target) nucleic acid molecule. On the other hand, cDNA or its fragment, synthesized DNA and the like may be used as a probe nucleic acid molecule. They are well known for those skilled in the art, and may be selected depending a kind of the method or apparatus of the electrochemical detection and the like.

High sequence-specificity may be attained in the electrochemical detection method according to the present invention by designing the present compound so that each pair of "V" and "X" located in the general formula (I) at a position corresponding to G/C and A/T (U) base pairs in subject double-stranded nucleic acid molecules shall be composed of imidazole derivative/pyrrole derivative and pyrrole derivative/pyrrole derivative, respectively.

Measurement principle in the electrochemical detection method according to the present invention is hybridization between the nucleic acid molecules, which may be carried out any method or operation known for those skilled in the art. For example, a method using DNA microarray (DNA chip)) may be listed as that with the use of hybridization on solid phase. The apparatus or device for the electrochemical detection per se such as an electrochemical chip or ECA chip is well known for those skilled in the art, which may be used in the method of the present invention. Said apparatus or device may be alternatively manufactured in accordance with a method well known for those skilled in the art.

The electric signal to be detected includes currency, electroconductivity, electric potential, electric capacity, inductance, and impedance, which may be detected with the apparatuses such as a cyclic voltammetry (CV), differential pulse voltammetry (DPV), linear sweep voltammography and potentiostat.

The method for electrochemical detection of double-stranded nucleic acid molecules according to the present invention with the use of the ligand of the present invention for the sequence-specific detection of double-stranded nucleic acid molecules may be utilized in various methods for detection based on the hybridization of the nucleic acids, including polymorphism analysis such as SNP, determination of base sequences, analysis of gene mutation, monitoring of gene expression and the like.

EXAMPLE

The present invention will be explained more in detail in line with the examples. Those skilled in the art may easily conceive other various examples having the features of the present invention based on the technical common knowledge in the art and on the description of the present specification, which shall therefore fall within the scope of the present invention as well.

Example 1

Synthesis of the Compound of the Formula (VIII)

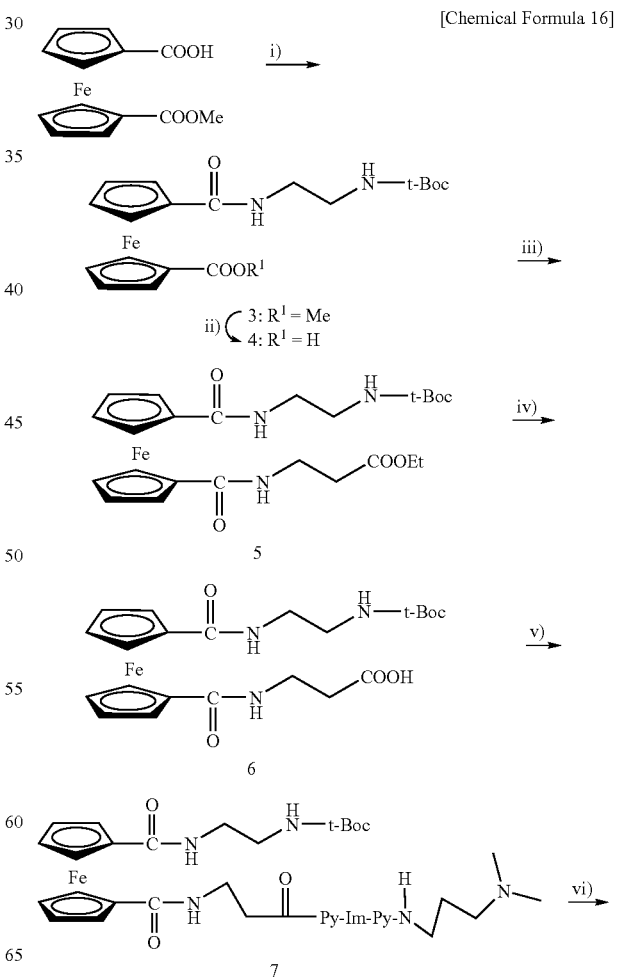

[Chemical Formula 16]

-continued

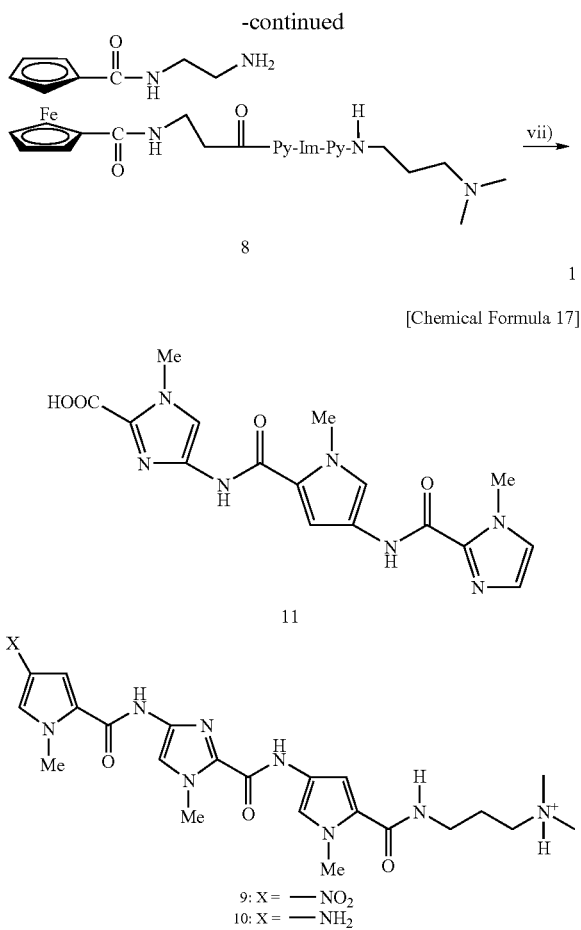

8

1

[Chemical Formula 17]

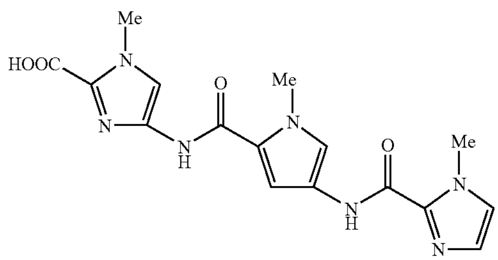

11

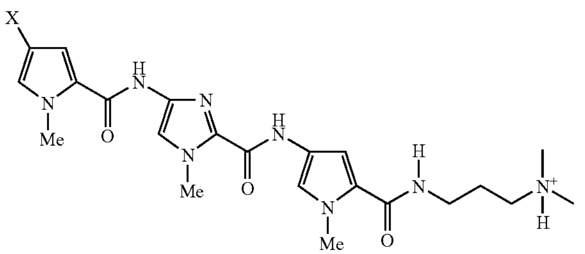

9: X = $-NO_2$
10: X = $-NH_2$

The structure of the above compounds was selected in view of availability of starting materials and chemical stability of the final and intermediate products. The sequence of the PIPA region was designed so as to bind to a target single base mutation in the human genome, which may be a factor determining interferon-resistance in a patient, i.e., CGC/GCG sequence.

Ferrocene methyl dicarboxylate (2) was condensed with N-t-butoxycarbonyl-1,3-propanediamine by means of 2-chloro-1-methylpyridinium iodide (CMPI) (Bald, E.; Saigo, K.; Mukaiyama, T. Chem. Lett. 1975, 1163-1166) with a yield of 87%. The resulting compound (3) was converted into its carboxylic acid (4) by the treatment with an alkaline aqueous solution, which was then condensed with ethyl 3-aminopropionate to give a ferrocene-binding unit (5) with a yield of 62%.

Ethyl ester of the above compound (5) was removed by the treatment with an alkaline aqueous solution for the introduction of pyrrole-imidazole moiety (yield: 93%). A free carboxyl group of the compound (6) was bound to 3-aminopyrrole derivative (10) that had been prepared in situ by hydrogenation of 3-nitropyrrole derivative (9) with CMPI to give a compound (7) (yield: 62%). The resulting compound (7) was further hydrolyzed by the treatment with 10% TFA in $CH_2Cl_2$ to give its amine (8) (yield: 71%).

The compound (8) (187.6 mg, 0.4777 mmol) was dissolved in methylene chloride (4.77 ml), to which were added diisopropylethylamine (0.162 ml, 0.947 mmol) and O-(benzotriazole-yl)-N,N,N',N'-tetramethyl uronium hexafuluorophosphate (361.8 mg, 0.954 mmol) as a condensing agent (Dourtoglou, V.; Ziegler, J.-C.; Gross, B. Tetrahedron Letters 1978, 15, 1269-1272, et al.), and stirred for 30 min at a room temperature. Methylene chloride (4.8 ml) dissolving a carboxylic acid (11) (400 mg, 0.477 mmol) prepared separately (Baird, E. E., Dervam, P. B. J. Am. Chem. Soc., 1996, 118, 6414-6416) was added to the above mixture and stirred for one hour. After the resulting mixture was washed with water, an organic layer was collected and dried over anhydrous sodium sulfate, so that the solvent was distilled out under a reduced pressure. The residue was purified with silica gel chromatography to give a final product (349 mg, 61%). The structure of the product was confirmed by $^1$H-NMR and $^{13}$C-NMR.

$^1$H-NMR (DMSO-d6) δ 1.59-1.65(2H, m), 2.15(6H, s), 2.26-2.28(2H, t, J=7.1 Hz), 2.56-2.59(2H, t, J=7.0 Hz), 3.18-3.22(2H, m,), 3.37-3.50(6H,m), 3.81(3H, s), 3.83(3H, s), 3.85 (3H, s), 3.94 (3H, s), 3.97 (3H, s), 3.99(3H, s), 4.27-4.30 (4H, m), 4.73(4H, s), 6.88(1H, d, J=1.7 Hz), 6.94(1H, d, J=1.5 Hz), 7.02(1H, s), 7.16(1H, d, J=1.7 Hz), 7.19(1H, d, J=1.5 Hz), 7.26(1H, d, J=1.7 Hz), 7.35-7.36(2H, m), 7.46(1H, s), 7.49(1H, s), 7.86-7,87(1H, t, J=5.6 Hz), 7.91-7.93(1H, t, J=5.5 Hz), 7.98-7.80(1H, t, J=5.5 Hz), 8.05-8.08(1H, t, J=5.7 Hz), 9.77(1H, s), 9.88(1H, s), 10.03(1H, s), 10.06(1H, s), 10.19(1H, s)

$^{13}$C-NMR (DMSO-d6) δ 27.2, 35.1, 35.1, 35.3, 36.0, 36.1, 36.2, 36.4, 36.5, 37.4, 38.8, 39.0, 45.3, 57.3, 69.8, 71.7, 71.8, 77.9, 78.0, 79.3, 104.1, 104.8, 106.1, 114.6, 114.9, 118.0, 119.4, 119.6, 121.4, 1221.7, 122.2, 122.3, 122.4, 123.5, 126.6, 127.2, 134.1, 134.4, 136.2, 138.9, 155.9, 156.3, 158.9, 158.9, 159.2, 161.2, 168.2, 168.6, 169.0 MS m/z calcd for C55H66FeN1909+: 1192.46403, found 1192.37089.

Similarly, the compound of the formula (IX) was synthesized in accordance with the following reaction scheme. The structure of the product was confirmed by $^1$H-NMR and $^{13}$C-NMR.

[Chemical Formula 18]

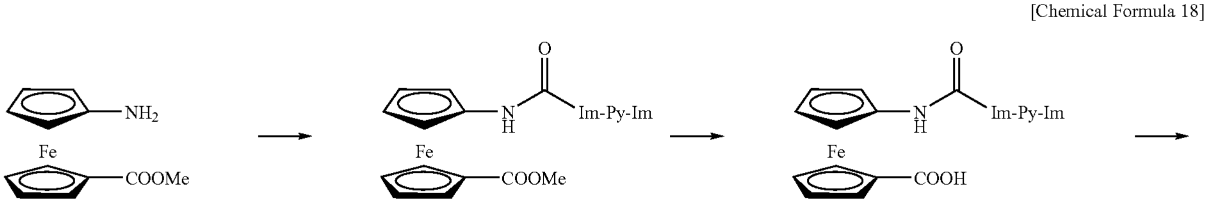

-continued

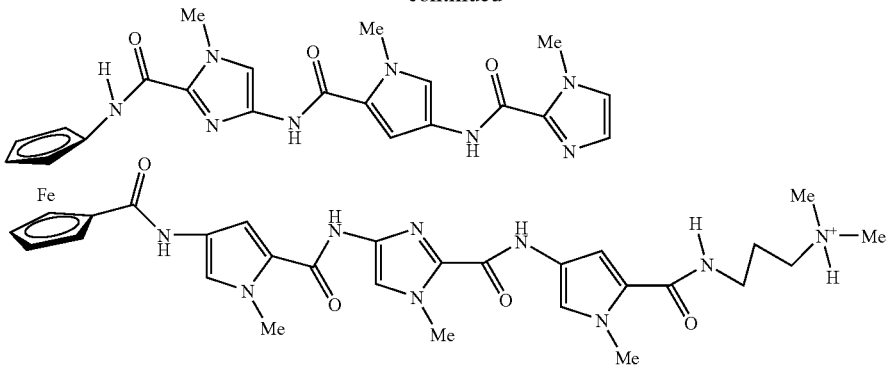

$^1$H-NMR (DMSO-d6) δ 1.57-1.63(2H, m), 2.13(6H, s), 2.22-2.25(2H,t, J=6.9 Hz), 3.16-3.20(2H,dd, J=6.9 Hz), 3.76 (3H, s), 3.79(3H, s), 3.82(3H, s), 3.85(3H, s), 3.96(3H, s), 3.99(3H, s), 4.04(3H, t, J=1.8 Hz), 4.35(3H,t, J=1.8 Hz), 4.85(3H, t, J=2.0 Hz), 4.95(3H, t, J=1.8 Hz), 6.88 (1H,d, J=1.7 Hz), 6.97 (1H, d, J=1.7 Hz), 7.03 (1H, d, J=1.0 Hz), 7.07 (1H,d, J=1.7 Hz), 7.19-7.20 (2H,m), 7.37 (1H, s), 7.38 (1H, s), 7.49 (1H, s), 7.52 (1H, s), 8.07-8.10(1H,t, J=5.6 Hz), 9.13(1H, s), 9.51 (1H,s), 9.90 (1H, s), 10.16 (1H, s), 10.25 (1H, s), 10.35 (1H, s)

$^{13}$C-NMR (DMSO-d6) δ 27.3, 33.6, 35.1, 35.3, 36.2, 36.4, 36.5, 37.4, 45.4, 57.4, 61.9, 65.7, 69.3, 71.1, 78.3, 79.4, 96.1, 104.1, 105.4, 106.1, 114.9, 115.0, 118.0, 119.7, 119.8, 121.3, 121.7, 121.8, 122.3, 122.4, 123.5, 126.6, 127.2, 133.9, 134.3, 136.2, 136.3, 138.9, 155.9, 156.3, 156.9, 158.9, 158.9, 161.2, 165.7

MS m/z calcd for C49H56FeN17O7+:1050.38980, found 1050.40297.

Example 2

Properties of the Compound of the Formula (VIII) As a Ligand

The binding of the above compound to a target DNA (TTTCTGCGGCCGGAG/CTCCGGC CGCAGAAA:Tm=67.1° C.) was detected with CD spectrum in order to confirm its utility as a ligand for the double-stranded helical DNA. The results in FIG. 1 show a CD profile in the titration of the above 15-mer DNA with 0, 0.2, 0.4, 0.6, 0.8, 1.0, 1.2 and 1.4 equivalents of the present compound. It is well known that elliptical polarization at 300-360 nm was induced by the interaction with a minor groove (Pilch, D. S.; Poklar, N.; Baird, E. E.; Dervan, P. B.; Breslauer, K. J. Biochemistry, 2002, 38, 2143-2151). As a result, the addition of the solution of the target DNA (5.0 μM) caused concentration-dependent increase of a positive cotton effect with an isosbestic point at 292 nm.

Next, the present compounds were further synthesized in accordance with the following reaction schemes:

[Chemical Formula 19]

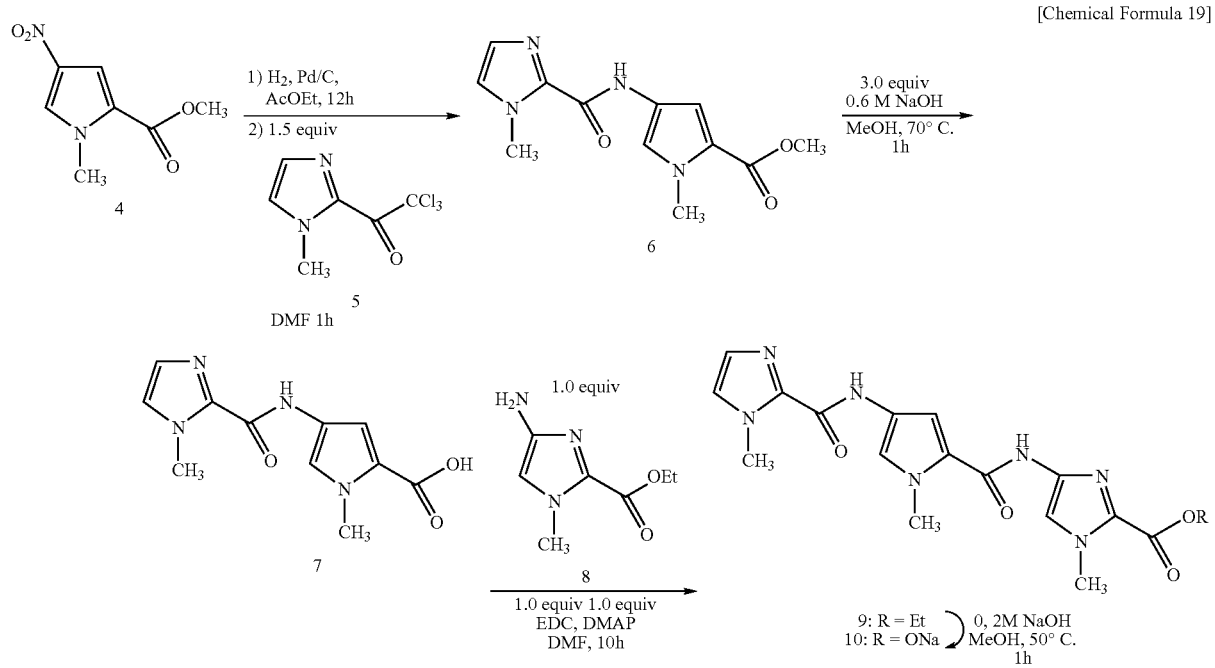

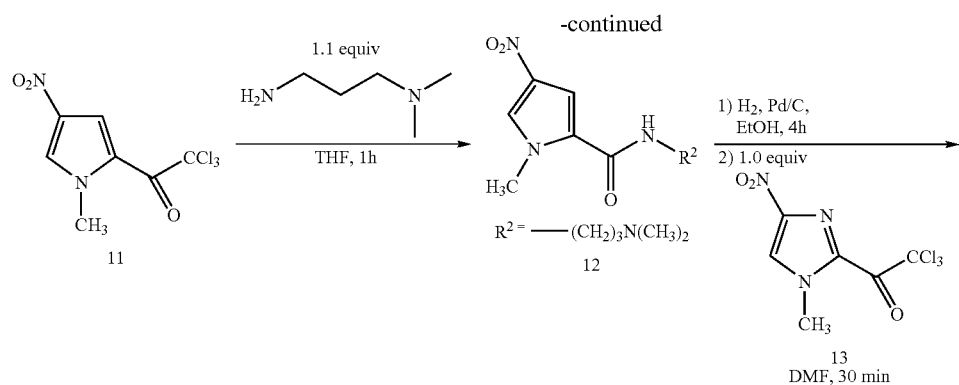
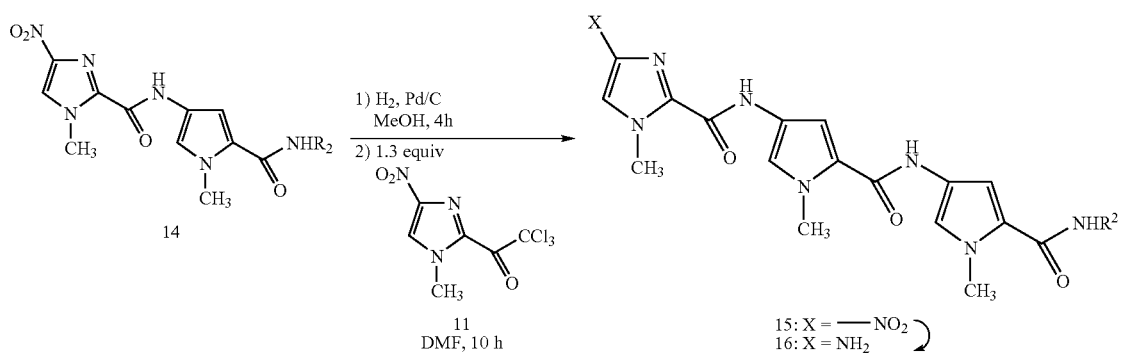
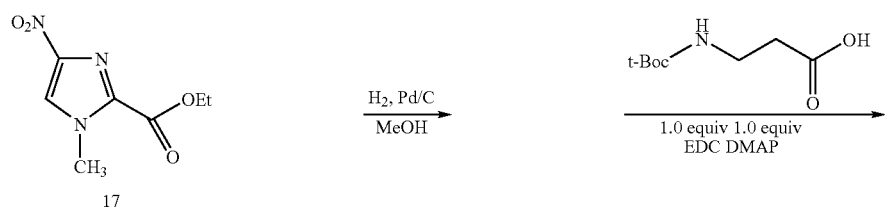
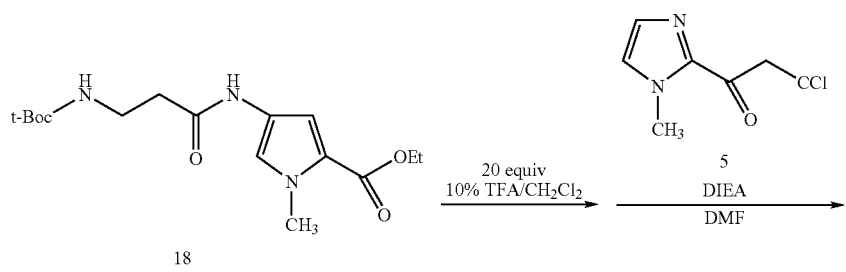
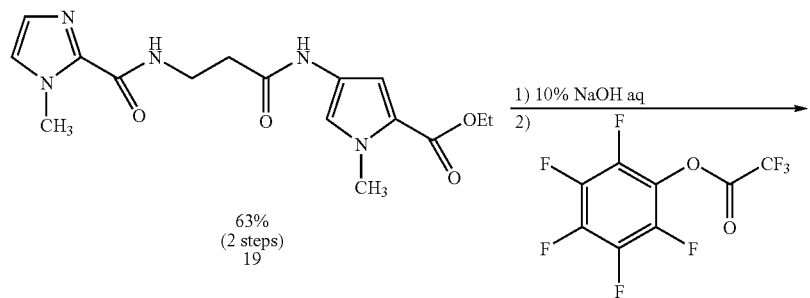

-continued
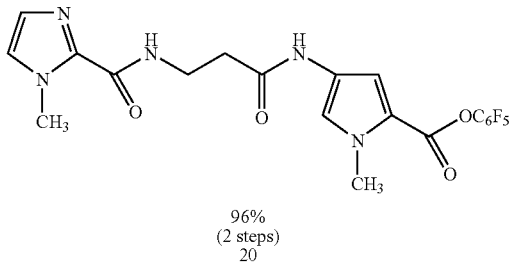
96%
(2 steps)
20
[Chemical Formula 20]
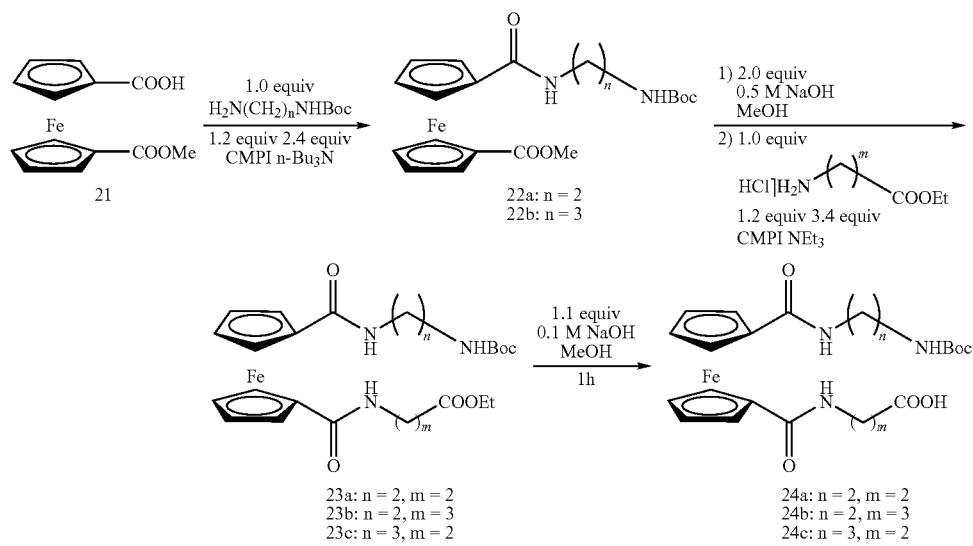
[Chemical Formula 21]
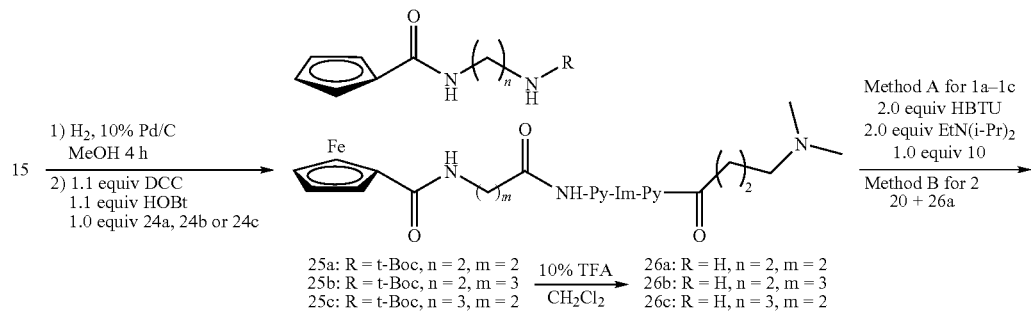
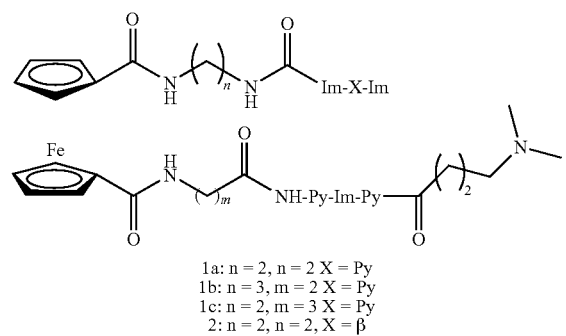
1a: n = 2, m = 2 X = Py
1b: n = 3, m = 2 X = Py
1c: n = 2, m = 3 X = Py
2: n = 2, n = 2, X = β

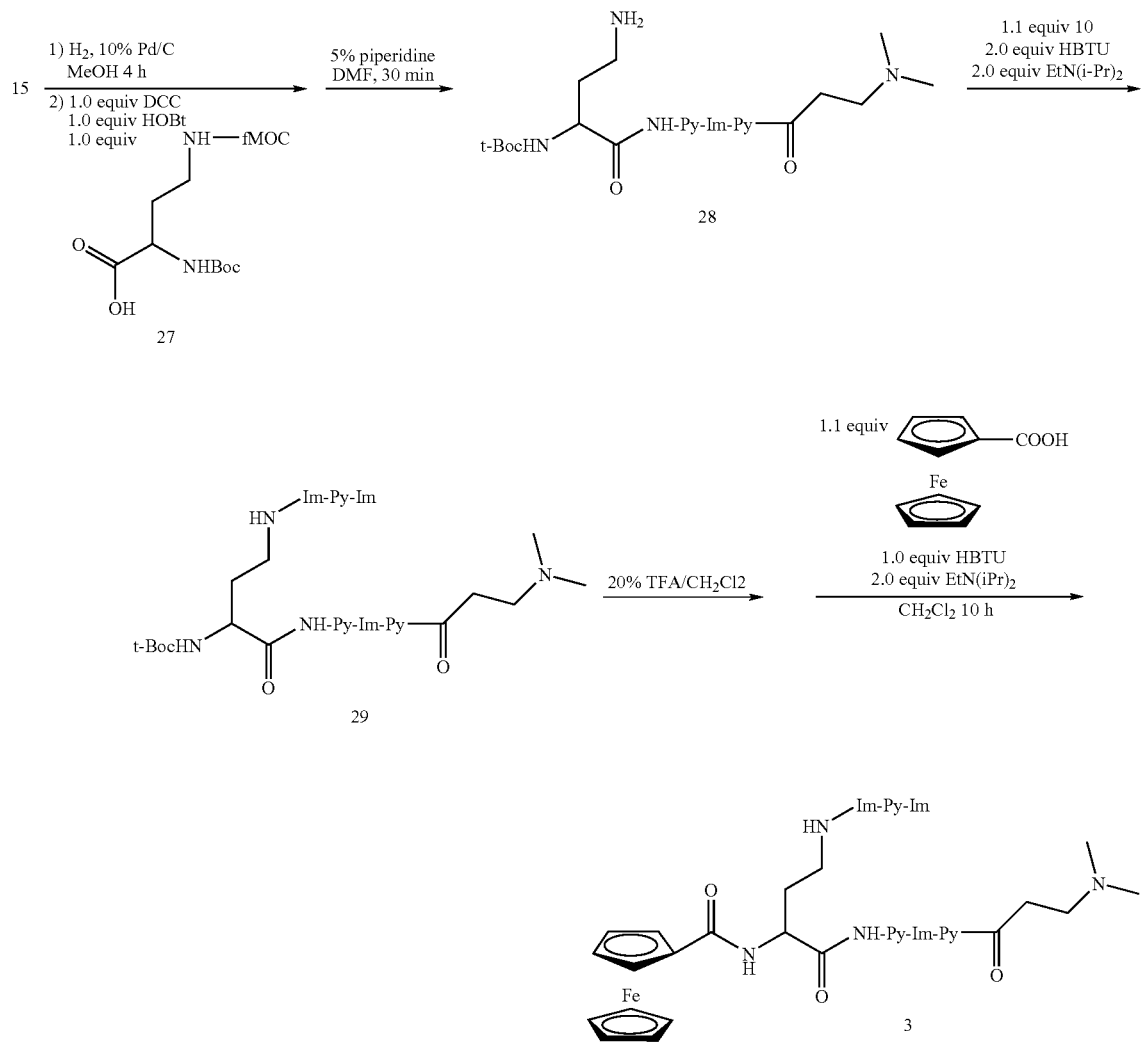

Synthesis Example 1 of the Material Compound

1-Methyl-4-(1-methylimidazole-2-carboxamido)pyrrole-2-carboxylic acid (7)

The compound 6 (8.8 g, 33.6 mmol) prepared from the compound 4 (Baird, E. E.; Dervan, P. B. *J. Org. Chem.* 1996, 118, 6141-6146) and the compound 5 (Nishiwaki, E.; Tanaka, S.; Lee, H.; Shibuya, M. *Heterocycles* 1988, 8, 1945-1952) by the methods described in the articles was dissolved in ethanol (234 mL), mixed with 0.6 M aqueous solution of sodium hydroxide (168 ml, 110.7 mmol) and stirred for one hour at 70° C. After being cooled to a room temperature, the resulting solution was mixed with hydrochloric acid (3N), so that white powder was generated at pH 3.0, which was then filtered to give the compound 9 (8.1 g, 97%).

$^1$HNMR (DMSO-d6) δ 3.82(3H, s), 3.97(3H, s), 6.97(1H, d, J=2.0 Hz), 7.03(1H, s), 7.38(1H, s), 7.47(1H, d, J=2.0 Hz), 10.48(1H, s), 12.19(1H, s); $^{13}$CNMR (DMSO-d6) δ 35.3, 36.4, 109.1, 119.9, 120.7, 122.1, 126.6, 127.2, 138.8, 156.3, 162.1. Anal. Calcd. for $C_{11}H_{12}N_4O_3$: C, 53.22; H, 4.89; N, 22.57. Found: C, 52.45; H, 4.72; N, 22.34.

Synthesis Example 2 of the Material Compound

2-Ethoxycarbonyl-1-methyl-4-{4-(1-methylimidazole-2-carboxamido)-1-methypyrrole-2-carboxamido}imidazole (9)

The compound 7 was dissolved in methanol (94.4 ml), mixed with 10% Pd/C (1.18 g) and stirred for four hours under hydrogen atmosphere. 10% Pd/C was removed from the reaction system with cerite filtration, so that the solvent was distilled out under a reduced pressure.

Dimethylformamide (10 ml) was added to the residue and distilled out again under a reduced pressure. The residue was dissolved in dimethylformamide (10 mL) again, and mixed with the compound 8 (5.9 g, 23.6 mmol) (Baird, E. E.; Dervan, P. B. *J. Org. Chem.* 1996, 118, 6141-6146), EDC (9.05 g, 47.2 mmol) and dimethylaminopyridine (288 mg, 2.36 mmol), and stirred for 12 hours at a room temperature. Re-precipitation treatment with chloroform and ethyl acetate gave the compound 9 as white powder (5.9 g, 63%).

$^1$HNMR (DMSO-d$_6$) δ 1.28-1.30(3H, t, J=7.1 Hz), 3.85 (3H, s), 3.93(3H, s), 3.98 (3H, s), 4.25-4.29 (2H, dd, J=7.1 Hz), 7.03(1H, d, J=0.7 Hz), 7.22(1H, d, J=2.0 Hz), 7.38(1H, s), 7.38(1H, s), 7.66(1H, s), 10.35(1H, s), 10.74 (1H, s); $^{13}$CNMR (DMSO-d$_6$) δ 14.3, 35.3, 35.7, 36.5, 60.8, 106.4, 115.6, 119.8, 121.6, 122.2, 126.5, 127.2, 131.0, 138.0, 139.0, 156.3, 158.7, 158.9: Anal. Calcd. for C$_{18}$H$_{12}$N$_4$O$_3$.H$_2$O: C, 53.22; H, 4.89; N, 22.57. Found: C, 50.88; H, 4.88; N, 23.13.

Synthesis Example 3 of the Material Compound

Sodium 1-methyl-4-{4-(1-methylimidazole-2-carboxamido)-1-methypyrrole-2-carboxamido}imidazole-2-carboxylate (10)

The compound 9 (3.0 g, 7.5 mmol) was dissolved in methanol (37.6 ml), mixed with aqueous solution of sodium hydroxide (37.6 ml, 7.89 mmol) and stirred for one hour at 50° C. After being cooled to a room temperature, the resulting solution was mixed with hydrochloric acid (1N) to reach pH 2.0, and then mixed with isopropylalcohol to give the white powder, which was then filtered to give the compound 10 (2.85 g, 94%).

$^1$HNMR (DMSO-d$_6$) δ 3.86(3H, s), 3.92(3H, s), 4.01(3H, s), 0.7.23 (1H, s), 7.25 (1H, s), 7.40 (1H, s), 7.52 (1H, s), 7.61 (1H, s), 10.70(1H, s), 10.71(1H, s); $^{13}$CNMR (DMSO-d$_6$) δ 25.6, 35.7, 36.5, 106.2, 115.3, 119.9, 121.3, 122.4, 125.1, 126.6, 131.9, 137.3, 138.1, 154.7, 158.8, 160.1. MS m/z calcd for C$_{16}$H$_{18}$N$_7$O$_4$+: 372.14203, found 394.11781[M+Na]$^+$.

Synthesis Example 4 of the Material Compound 2-(3-Dimethylaminopropyl)aminocarbonyl-1-methyl-4-nitropyrrole (12)

The compound 11 (25 g, 92 mmol) disclosed in the article (Nishiwaki, E.; Tanaka, S.; Lee, H.; Shibuya, M. *Heterocycles* 1988, 8, 1945-1952) was added dropwise to THF (10 ml) dissolving 3-dimethylaminopropylamine (12.6 g, 101 mmol) at 0° C. After being heated to a room temperature, the resulting solution was stirred for one hour, and the solvent was distilled out. Re-crystallization of the residue with methanol gave the compound 12 (19.6 g, 84%).

$^1$HNMR (DMSO-d$_6$) δ 1.6(t,J=7.1 Hz), 2.1(6H,s), 2.2(2H, t;J=7.1 Hz), 3.2(2H,q,J=7.1 Hz) 3.9(3H,s), 7.9(1H,s), 8.1 (1H,s), 8.4(1H,t,J=5.5 Hz).

Synthesis Example 5 of the Material Compound

1-Methyl-4-(1-methyl-4-nitroimidazole-2-carboxamido)-2-(3-dimethylaminopropylaminocarbonyl) pyrrole (14)

The compound 12 (2.8 g, 10.9 mmol) was dissolved in methanol (44 mL), mixed with 10% Pd/C (545 mg) and stirred under hydrogen atmosphere for four hours at a room temperature. 10% Pd/C was filtered out, and the solvent was distilled out. The residue was dissolved in dimethylformamide (10 mL), followed by azeotropy to reduce its volume by half so as to remove methanol. The known compound 13 (3.0 g, 10.9 mmol) dissolved in DMF (10 ml) was added to the resulting solution at 0° C. After being heated to a room temperature, the solvent was distilled out and the residue was washed with 2-propanol to give the compound 14 (3.68 g, 90%).

$^1$HNMR (DMSO-d$_6$) δ 1.6 (2H, t,J=7.1 Hz), 2.1(6H, s), 2.2(2H, t; J=7.1 Hz), 3.2(2H, m), 3.8(3H, s), 4.0(3H, s), 7.0(1H, d, J=1.7 Hz), 7.3(1H, d, J=1.7 Hz), 8.1(1H, t, J=5.5 Hz), 8.6(1H, s), 10.8(1H, s).

Synthesis Example 6 of the Material Compound

1-Methyl-4-{1-methyl-4-(1-methyl-4-nitropyrole-2-carboxamido)imidazole-2-carboxamido}-2-(3-dimethylaminopropylaminocarbonyl) pyrrole (15)

The compound 14 (3.6 g, 9.6 mmol) was dissolved in methanol (38 mL), mixed with 10% Pd/C (481 mg) and stirred under hydrogen atmosphere for four hours at a room temperature. 10% Pd/C was filtered out, and the solvent was distilled out. The residue was dissolved in DMF (10 mL), followed by azeotropy to reduce its volume by half so as to remove methanol. The compound 11 (2.6 g, 9.6 mmol) dissolved in DMF (10 ml) was added to the resulting solution at 0° C. After being heated to a room temperature, the solvent was distilled out and the residue was washed with 2-propanol to give the compound 15 (3.5 g, 74%).

$^1$HNMR (DMSO-d$_6$) δ 1.74-1.77(2H, t, J=6.1 Hz), 2.27 (6H, s), 2.43-2.46(2H, t, J=6.1 Hz), 3.49-3.53(2H, m), 3.86 (3H, s), 4.05(6H, s), 6.57(1H, s), 7.16(1H, s), 7.27(1H, s), 7.44(1H, s), 7.61(1H, s), 7.69(1H, s), 7.90(1H, m), 8.58(1H, s), 9.25(1H, s).

Synthesis Example 7 of the Material Compound

2-Ethoxycarbonyl-1-methyl-4-{3-(tert-butoxycarbonylamino)propanamido}pyrrole (18)

The compound 17 (546 mg, 2.7 mmol) disclosed in Baird, E. E.; Dervan, P. B. *J. Org. Chem.* 1996, 118, 6141-6146 wa dissolved in methanol (11 ml), mixed with 10% Pd/C (137 mg) and stirred under hydrogen atmosphere for one hour and half at a room temperature. 10% Pd/C was filtered out, and the solvent was distilled out. The residue was dissolved in methylene chloride, mixed with N-(tert-butoxycarbonyl)-β-alanine (518 mg, 2.7 mmol), 1-(3-dimethylaminopropyl)-3-ethylcarboxydiimide hydrochloride (578 mg, 3.0 mmol), and 1-hydroxybenzotriazole (407 mg, 3.0 mmol) and stirred for two hours at a room temperature. The resulting solution was extracted with ethyl acetate (50 ml) and water (50 mL), dehydrated over sodium sulfate and concentrated under a reduce pressure. The resulting residue was purified with silica gel column (11 g) to give the compound 18 (510 mg, 56%).

$^1$HNMR (DMSO) δ 1.27-1.30 (2H, t, J=7.2 Hz), 1.36(9H, s), 2.40-2.43(2H, t, J=7.2 z), 3.16-3.20(2H, m), 3.90(3H, s), 4.23-4.28(2H, q, J=7.1 Hz), 6.78(1H, m), 7.51(1H, s), 10.6 (1H, s).

Synthesis Example 8 of the Material Compound

2-Ethoxycarbonyl-1-methyl-4-{3-(1-methylmidazole-2-carboxamido)propanamido}pyrrole (19)

The compound 18 (510 mg, 1.5 mmol) was mixed with 10% trifluoroacetic acid/methylene chloride (24 mL, 30 mmol) and stirred for one hour at a room temperature. The resulting solution was washed with water (15 mL), dehydrated over sodium sulfate, filtered and concentrated. The resulting residue was dissolved in DMF, mixed with N,N'-diisopropylamine (128 μl, 0.75 mmol) and the compound 5 (490 mg, 1.8 mmol) and stirred for two hours at a room temperature. The resulting solution was extracted with chloroform (30 ml) and water (20 mL), dehydrated over sodium sulfate and concentrated. Re-precipitation of the resulting residue from chloroform and diisopropylether gave the compound 19 (475 mg, 91%).

$^1$HNMR (DMSO-d$_6$) δ 1.26-1.28 (3H, t, J=7.1 Hz), 2.53-2.56(2H, t, J=6.8 Hz), 3.45-3.49(2H, m), 3.89(3H, s), 3.92 (3H, s), 4.22-4.26(2H, m), 6.94(1H, s), 7.31(1H, s), 7.53(1H, s), 8.34(1H, m), 10.7(1H, s).

Synthesis Example 9 of the Material Compound 2-pentafluorophenoxycarbonyl-1-methyl-4-{3-(1-methylmidazole-2-carboxamido)propanamido}pyrrole (20)

The compound 19 (65 mg, 0.19 mmol) was dissolved in methanol (19 mL), mixed with aqueous solution of sodium hydroxide (0.4 M) (1.4 mL, 0.56 mmol) and stirred for one hour at 50° C. After being cooled to a room temperature, the solution was adjusted to pH 2 with 1 M hydrochloric acid. The precipitated powder was washed with 2-propanol, and the solvent was distilled out. The residue was dissolved in DMF (1.3 mL), mixed with pentafluorophenyltrifluoromethyl acetate (68 μL, 0.39 mmol) and pyridine (32 μL, 0.39 mmol), and stirred under argon atmosphere for one hour at a room temperature. The solution was washed with 0.1 M hydrochloric acid (10 mL×3), 5% aqueous solution of sodium hydrogen carbonate (10 ml) and saturated saline (10 mL), and dehydrated over sodium sulfate. The residue was concentrated under a reduced pressure to give the compound 20 (88 mg, 96%).

$^1$HNMR (DMSO-d$_6$) δ 2.58-2.61(2H, t, J=7.0 Hz), 3.49-3.53(2H, m), 3.94(3H, s), 3.98(3H, s), 6.96(1H, d, J=1.0 Hz), 7.37(1H, d, J=0.6 Hz), 8.37-8.39(1H, t, J=6.0 Hz), 10.9(1H, s).

Synthesis Example 10 of the Material Compounds

A General Synthesis Method of Ferrocene Derivatives (22a) and (22b)

The compound 21 (1.0 g, 3.47 mmol) was dissolved in methylene chloride (35 ml), and mixed with N-tert-butoxycarbonylethylenediamine (0.56 g, 3.47 mmol), n-tributylamine (2.0 mL, 8.3 mmol) and 2-chloro-1-methyl pyridinium iodide (1.1 g, 4.16 mmol). The mixture was washed with water (20 ml) and saturated saline, dehydrated over sodium sulfate and concentrated under a reduced pressure. The residue was purified with column chromatography to give the compound (22a) (1.3 g, 87%).

22a:
$^1$HNMR (DMSO-d$_6$) δ 1.37(9H, s), 3.09(2H, m), 3.72(3H, s), 4.38-4.80(8H, s), 6.85(1H, t), 7.84(1H, t).

Synthesis of (22b)

The compound (22b) was prepared by the same method as for the compound (22a) using N-tert-butoxycarbonylpropylenediamine instead of N-tert-butoxycarbonylethylenediamine.

22b:
$^1$HNMR (DMSO-d$_6$) δ 1.38 (9H, s), 1.57-1.63 (2H, m, J=6.8, 7.1 Hz), 2.97-3.01 (2H, q, J=6.3, 6.6 Hz), 3.14-3.18 (2H, q, J=6.3 Hz), 3.72 (3H, s), 4.37-4.44 (4H, m), 4.71-4.81 (4H, m), 6.81-6.83 (1H, t, J=5.6 Hz), 7.77-7.80 (1H, t, J=5.6 Hz),

Synthesis Example 11 of the Material Compounds

A General Synthesis Method of Ferrocene Derivatives (23a), (23b) and (23c)

The compound (22a) (10.5 g, 20 mmol) was dissolved in methanol (200 mL), mixed with aqueous solution of sodium hydroxide (0.5 M) (200 mL, 40 mmol) and stirred for 12 hours at 80° C. After being cooled to a room temperature, the solution was adjusted to pH 3.0 with citric acid and washed with water. The resulting organic layer was collected and dehydrated with anhydrous sodium sulfate, and the solvent was distilled out under a reduced pressure. The residue was dissolved in methylene chloride (220 ml), and mixed with ethyl ester hydrochloride of β-alanine (3.5 g, 22.8 mmol), triethylamine (10.8 ml, 77.5 mmol) and 2-chloro-1-methyliodide (6.7 g, 27.4 mmol) under argon atmosphere. After being stirred for two hours at a room temperature, the solution was washed with water. The resulting organic layer was collected and dehydrated with anhydrous sodium sulfate. The solvent was distilled out under a reduced pressure, and the residue was purified with silica gel chromatography to give the compound (23a) (8.7 g, 85%)

$^1$HNMR(CDCl$_3$) δ 1.18-1.21(3H, t, J=7.1 Hz) 1.32(9H, s), 2.59-2.61(2H, t, J=6.3 Hz), 3.32(2H, m), 3.42-3.45(2H, dd, J=5.4 Hz), 3.57-3.60 (2H, dd, J=6.3 Hz), 4.07-4.12 (2H, dd, J=7.1 Hz), 4.27(3H, t, J=2.0 Hz), 4.29-4.30(3H, t, J=1.8 Hz), 4.46(4H, d, J=1.5 Hz), 5.89(1H, m), 7.34-7.37(1H, t, J=1.8 Hz), 7.55-7.57(1H, t, J=1.8 Hz); $^{13}$CNMR(CDCl$_3$) δ 14.0, 28.2, 33.9, 35.3, 40.2, 40.5, 60.4, 70.4, 70.5, 70.9, 71.0, 77.6, 78.0, 78.9, 156.5, 170.4, 170.5, 172.2 MS m/z calcd for C$_{23}$H$_{34}$FeN$_3$O$_6$$^+$: 516.17970, found 516.23203.

The compounds (23b) and (23c) were obtained by reacting the compounds (22a) and (22b), respectively, with an appropriate ester of an amino acid in accordance with the above general synthesis method.

23b:
$^1$H NMR (500 MHz, DMSO) δ 1.16-1.19 (3H, t, j=7.1 Hz), 1.38 (9H, s), 1.75-1.78 (2H, m, j=7.1 Hz), 2.35-2.38 (2H, m), 3.09-3.11 (2H, m, j=5.9, 6.1 Hz), 3.18-3.23 (2H, q, j=5.9, 6.1, 6.6 Hz), 4.03-4.08 (2H, q, j=7.1 Hz), 4.29-4.31 (4H, m), 4.69-4.72 (4H, m), 6.90 (1H, t), 7.86-7.88 (1H, t, j=5.6 Hz), 7.90-7.92 (1H, t. j=5.6 Hz)

23c:
$^1$H NMR (500 MHz, DMSO) δ 1.18-1.21 (3H, t, j=7.1 Hz), 1.38 (9H, s), 1.59-1.62 (2H, m, j=7.1 Hz), 2.56-2.59 (2H, t, j=6.8 Hz), 2.97-3.01 (2H, q, j=6.6 Hz), 3.15-3.19 (2H, q, j=6.6, 6.8 Hz), 3.39-3.43 (2H, q, j=6.6, 7.1 Hz), 4.07-4.11 (2H q, j=7.1 Hz), 4.28-4.30 (4H, m,), 4.69-4.70 (4H, m), 6.81-6.83 (1H, t), 7.82-7.85 (1H, t, j=5.9 Hz) 7.96-7.98 (1H, t, j=5.8 Hz)

Synthesis Example 12 of the Material Compounds

A General Synthesis Method of Ferrocene Derivatives (24a), (24b) and (24c)

The compound (23a) (2.0 g, 3.38 mmol) was dissolved in methanol (39 mL), mixed with aqueous solution of sodium hydroxide (0.1 M) (41 mL, 4.07 mmol) and stirred for 12 hours at a room temperature. The solution was adjusted to pH 3.0 with 1 N hydrochloric acid and washed with water. The resulting organic layer was collected and dehydrated with anhydrous sodium sulfate, so that the solvent was distilled out under a reduced pressure. The residue was purified with silica gel chromatography to give the compound (24a) (1.84 g, 97%).

$^1$HNMR (DMSO-d$_6$) δ 1.37 (9H, s), 2.49-2.53(2H, m), 3.07-3.10(2H, dd, J=6.1 Hz), 3.19-3.22 (2H, dd, J=6.1 Hz), 3.36-3.40 (2H, dd, J=6.3 Hz), 4.28-4.29(4H, t, J=1.7 Hz), 4.69-4.71(4H, m), 6.91-6.94(1H, t, J=5.6 Hz), 7.83-7.86(1H, t, J=5.7 Hz), 7.93-7.95(1H, t, J=5.4 Hz), 12.25 (1H, s); $^{13}$CNMR (DMSO-d$_6$) δ 28.5, 34.3, 35.5, 38.8, 69.8, 71.7, 71.8, 72.2, 77.8, 77.8, 77.9, 79.4, 155.9, 168.7, 168.8, 173.3. MS m/z calcd for C$_{22}$H$_{30}$FeN$_3$O$_6$$^+$: 488.14840, found 488.22584.

The compounds (24b) and (24c) were obtained by using the compounds (23b) and (23c), respectively, as a starting material in accordance with the above general synthesis method.

24b:
$^1$H NMR (500 MHz, DMSO) δ 1.38 (9H, s), 1.72-1.77 (2H, m, J=7.1, 7.3 Hz), 2.28-2.31 (2H, t, J=7.3 Hz), 3.08-3.11 (2H, q, J=6.3 Hz), 3.18-3.24 (4H, m, J=6.3 Hz), 4.29-4.30 (4H, s), 4.69-4.72 (4H, m), 6.91-6.93 (1H, t, J=5.6 Hz), 7.87-7.92 (2H, m, J=5.6, 5.8 Hz), 12.1 (1H, s)

24c:
$^1$H NMR (500 MHz, DMSO) δ 1.38 (9H, s), 1.59-1.63 (2H, m, J=6.8 Hz), 2.97-3.01 (2H, m, J=6.6 Hz), 3.15-3.19 (2H, q, J=6.6, 6.8 Hz), 3.36-3.40 (2H, m, J=6.8 Hz), 4.28-4.29 (4H, t), 4.70-4.72 (4H, m), 6.81-6.83 (1H, t, J=5.6 Hz), 7.81-7.83 (1H, t, J=5.9 Hz), 7.92-7.94 (1H, t, J=5.4 Hz), 12.2 (1H, s).

Synthesis Example 13 of the Material Compounds

A General Synthesis Method of Ferrocene Derivatives (25a), (25b) and (25c)

The compound 15 (1.64 g, 3.28 mmol) was dissolved in methanol (13.1 mL), mixed with 10% Pd/C (164 mg) and stirred under hydrogen atmosphere for four hours. 10% Pd/C was removed by filtration with cerite, and the solvent was distilled out under a reduced pressure. The residue was dissolved in methylene chloride (32.8 ml), mixed with the compound (24a) (1.60 g, 3.28 mmol), DCC (744 mg, 3.61 mmol) and hydroxybenzotriazole (488 mg, 3.61 mmol), and stirred for one hour at a room temperature. The precipitated white powder was filtered out and washed with water. An organic layer was collected and dehydrated with anhydrous sodium sulfate, so that the solvent was distilled out under a reduced pressure. The residue was purified with silica gel chromatography to give the compound (25a) (2.52 g, 82

$^1$HNMR (DMSO-d$_6$) δ 1.37(9H, s), 1.70-1.73(2H, t, J=7.1 Hz), 2.42(6H, s), 2.55-2.61(4H, m), 3.09-3.47(16H, m), 3.80 (3H, s), 3.83(3H, s), 3.95(3H, s), 4.28-4.29(4H, m), 4.71-4.73 (4H, m), 6.92 (1H, d, J=1.5 Hz), 6.94 (1H, d, J=1.7 Hz), 7.21(1H, d, J=1.7 Hz), 7.29(1H, d, J=1.5 Hz), 7.51(1H, s), 7.88-7.91(1H, t, J=5.5 Hz), 8.00-8.01(1H, t, J=5.5 Hz), 8.14-8.16(1H, t, J=5.4 Hz), 8.31(1H, s), 9.95(1H, s), 10.23(1H, s); $^{13}$CNMR (DMSO-d$_6$) δ 26.1, 28.4, 35.0, 36.0, 36.0, 36.2, 36.4, 36.6, 43.9, 56.2, 69.8, 71.7, 77.8, 77.9, 79.3, 104.3, 104.8, 114.9, 118.1, 119.3, 121.4, 122.0, 122.3, 123.3, 134.3, 136.2, 155.9, 158.8, 161.4, 168.1, 168.7, 168.8. MS m/z calcd for C$_{44}$H$_{59}$FeN$_{12}$O$_8$$^+$: 939.39282, found 939.2523.

The compounds (25b) and (25c) were obtained by using the compounds (24b) and (24c), respectively, as a starting material in accordance with the above general synthesis method.

25b:
$^1$H NMR (500 MHz, DMSO) δ 1.38 (9H, s), 1.59-1.63 (2H, m, j=7.1 Hz), 1.81-1.84 (2H, m, j=7.3 Hz), 2.14 (6H, s), 2.23-2.26 (2H, t, j=7.1 Hz), 2.31-2.34 (2H, m, j=7.3 Hz), 3.09-3.12 (2H, m, j=5.9 Hz), 3.17-3.25 (6H, m), 3.80 (3H, s), 3.84 (3H, s), 3.97 (3H, s), 4.32 (4H, s), 4.70-4.73 (4H, m), 6.89-6.93 (3H, m, j=1.7, 1.9 Hz), 7.22 (1H, d, j=1.7 Hz), 7.28 (1H, d, j=1.7 Hz), 7.53 (1H, s), 7.89-7.94 (2H, m, j=5.6, 5.9 Hz), 8.09-8.11 (1H, t, j=5.6 Hz) 9.88 (1H, s), 9.95 (1H, s), 10.22 (1H, s)

25c:
$^1$H NMR (500 MHz, DMSO) δ 1.38 (9H, s), 1.58-1.64 (4H, m, j=6.8, 7,1 Hz), 2.14 (6H, s), 2.23-2.26 (2H, t, j=7.1 Hz), 2.56-2.58 (2H, t, j=7.1 Hz), 2.98-3.02 (2H, m, j=6.3, 6.6 Hz), 3.16-3.21 (4H, m, j=6.3, 6.6 Hz), 3.43-3.47 (2H, m, j=6.6, 6.8 Hz), 3.80 (3H, s), 3.84 (3H, s), 3.97 (3H, s), 4.28-4.29 (4H, m), 4.71-4.73 (4H, m) 6.81-6.83 (1H, t, j=5.6 Hz), 6.89 (1H, d, j=2.0 Hz), 6.93 (1H, d, j=2.0 Hz), 7.22 (1H, d, j=1.7 Hz), 7.30 (1H, d, j=1.7 Hz), 7.52 (1H, s) 7.83-7.85 (1H, t, j=5.9 Hz), 7.96-7.97 (1H, t, j=5.6 Hz), 8.08-8.11 (1H, t, j=5.6 Hz), 9.95 (1H, s), 9.97 (1H, s), 10.23 (1H, s).

Synthesis Example 14 of the Material Compounds

A General Synthesis Method of Ferrocene Derivatives (26a), (26b) and (26c)

The compound (25a) (1.5 g, 1.6 mmol) was dissolved in 10% trifluoro acetic acid/methylenechloride (25.3 ml, 32 mmol) and stirred for 5 hours at a room temperature. The solution was washed with water. An organic layer was collected and dehydrated with anhydrous sodium sulfate, so that the solvent was distilled out under a reduced pressure. The residue was purified with silica gel chromatography to give the compound (26a) (1.04 g, 78%).

$^1$HNMR(CDCl$_3$) δ 1.66-1.71(2H, m), 2.20(6H, s), 2.35-2.38(2H, t, J=Hz), 2.74(2H, s), 2.97(2H, m), 3.39-3.40(2H, m), 3.47(2H, m), 3.69(2H, s), 3.84(3H, s), 3.87(3H, s), 3.97 (3H, s), 4.27(2H, s), 4.31(2H, s), 4.58-4.60(4H, d, J=), 6.70 (1H, s), 6.90 (1H, s), 7.20 (1H, s), 7.23 (1H, s), 7.38 (1H, s), 7.45-7.46(1H, m), 7.76(2H, m), 7.83(1H, m), 9.07(1H, br), 9.21 (1H, br), 9.88 (1H, s); MS m/z calcd for C$_{39}$H$_{51}$FeN$_{12}$O$_6$$^+$: 839.34039, found 839.33831.

The compounds (26b) and (26c) were obtained by using the compounds (25b) and (25c), respectively, as a starting material in accordance with the above general synthesis method.

26b:
$^1$H NMR (500 MHz, DMSO) δ 1.58-1.64 (2H, m, j=7.1 Hz), 1.80-1.85 (2H, m), 2.14 (6H, s), 2.23-2.27 (2H, t, j=7.1 Hz), 2.31-2.36 (2H, m, j=7.1 Hz), 2.69-2.72 (2H, t, j=6.6 Hz), 3.17-3.23 (6H, m), 3.81 (3H, s), 3.84 (3H, s), 3.97 (3H, s), 4.29-4.33 (4H, m), 4.70-4.73 (4H, m) 6.88 (1H, s), 6.93 (1H, s), 7.22 (1H, s), 7.29 (1H, m), 7.53 (1H, s), 7.86-7.88 (1H, t, j=5.6 Hz), 7.92-7.97 (2H, m), 8.10-8.12 (1H, t, j=5.6 Hz), 9.90-9.91 (1H, d), 9.97 (1H, s)

26c:
$^1$H NMR (500 MHz, DMSO) δ 1.59-1.62 (4H, m), 2.14 (6H, s), 2.23-2.26 (2H, t, j=7.1 Hz), 2.57-2.59 (2H, t), 3.19-3.20 (2H, m), 3.24-3.25 (2H, m), 3.45-3.47 (2H, m), 3.80 (3H, s), 3.84 (3H, s), 3.97 (3H, s), 4.29 (4H, s), 4.71 (4H, d) 6.89 (1H, d, j=1.5 Hz), 6.94 (1H, s), 7.22 (1H, s), 7.30 (1H, s), 7.53 (1H, s), 7.93-7.95 (1H, t, j=5.4 Hz) 7.99-8.10 (2H, m, j=5.1 Hz), 9.99-10.02 (1H, m, j=5.1 Hz).

Synthesis Example 15 of the Material Compound

Polyamide (28)

The compound 15 (806 mg, 1.61 mmol) was dissolved in methanol (6.5 mL), mixed with 10% Pd/C (80.5 mg) and stirred under hydrogen atmosphere for four hours. 10% Pd/C was removed by filtration with cerite, and the solvent was distilled out under a reduced pressure. The residue was dissolved in methylene chloride (16 ml), mixed with 2-N-Boc-4-N-Fmoc-2,4-diaminobutylic acid (710 mg, 1.61 mmol), DCC (332.2 mg, 1.61 mmol) and hydroxybenzotriazole (217.5 mg, 1.61 mmol), and stirred for one hour at a room temperature. The precipitated white powder was filtered out, mixed with 5% piperidine/dimethylformamide (27.7 ml, 16.1 mol), stirred for 30 min at a room temperature and washed with water. An organic layer was collected and dehydrated with anhydrous sodium sulfate, so that the solvent was distilled out under a reduced pressure. The residue was purified with silica gel chromatography to give the compound (28) (453 mg, 42%).

$^1$HNMR(CDCl$_3$) δ 1.44 (9H, s), 1.71-1.76(2H, t, J=6.3 Hz), 1.91-1.98 (2H, t, J=6.3 Hz), 2.26(6H, s), 2.41-2.44 (2H, t, J=6.3 Hz), 2.90-2.95(2H, m), 3.44-3.47 (2H, dd, J=5.7 Hz), 3.83(3H, s), 3.91(3H, s), 4.01(3H, s), 4.52(1H, s), 6.46(1H, s), 6.63(1H, s), 6.67(1H, s), 7.15(1H, s), 7.26(1H, s), 7.37 (1H, s), 7.77 (1H, s), 8.24 (1H, s), 9.10 (1H, s), 9.64(1H, s). MS m/z calcd for $C_{31}H_{48}N_{11}O_6^+$: 670.37890, found 670.33883.

Synthesis Example 16 of the Material Compound

Polyamide (29)

The compound (10) (303.6 mg, 0.772 mmol) dissolved in methylene chloride (7.0 ml) was mixed with diisopropylethylamine (0.239 ml, 1.404 mmol) and O-(benzotriazole-yl)-N,N,N',N'-tetramethyluronium hexafluorophosphate (532.5 mg, 1.404 mmol), and stirred for 30 min at a room temperature. The compound (19) (470 mg, 0.702 mmol) dissolved in methylene chloride (7.0 ml) was added to the resulting solution and stirred for one hour. The resulting mixture was washed with water. An organic layer was collected and dehydrated with anhydrous sodium sulfate, so that the solvent was distilled out under a reduced pressure. The residue was re-precipitated from chloroform and diethylether to give the compound (29) (673 mg, 94%).

$^1$HNMR (DMSO-d$_6$)δ 1.34 (9H,s), 1.70-1.73(2H,t,), 1.75-193(2H,m), 2.41(6H,s), 2.61(2H.m), 3.19-3.22 (2H,dd, J=1.7 Hz), 3.27-3.37 (2H,m), 3.80 (3H,s), 3.83(3H,s), 3.85(3H,s), 3.92(3H,s), 3.96(3H,s), 3.98 (3H,s), 4.08-4.13 (1H,m) 6.94 (1H,d, J=1.5 Hz), 6.97 (1H, s), 7.02(1H,s), 7.16(1H,d, J=1.5 Hz), 7.22(1H,s), 7.26 (1H,d, J=1.2 Hz), 7.37 (1H,s), 7.38 (1H,d, J=1.5 Hz), 7.49(1H,s), 7.53(1H,s), 7.97-7.80(1H,t, J=5.5 Hz), 8.15-8.17(1H,t, J=5.5 Hz), 9.94(1H,s), 9.99(1H, s), 10.27(1H,s), 10.34(1H,s), 10.36(1H,s); $^{13}$CNMR (DMSO-d$_6$) δ 26.1, 28.4, 32.2, 35.1, 35.3, 35.7, 36.3, 36.4, 36.5, 36.6, 38.4, 43.9, 52.6, 56.1, 78.4, 79.4, 104.4, 105.0, 106.1, 114.5, 115.0, 118.2, 119.5, 119.7, 121.4, 121.7, 121.9, 122.1, 122.4, 123.3, 126.6, 127.2, 134.2, 134.4, 136.2, 136.2, 138.9, 155.6, 155.9, 156.3, 158.9, 158.9, 161.4, 169.4. MS m/z calcd for $C_{47}H_{63}N_{18}O_9^+$: 1023.50254, found 1023.49821.

Example 3

General Synthesis Method of the Compounds (1a) (1b), (1c) and (2)

The compound (26a) (187.6 mg, 0.477 mmol) dissolved in methylene chloride (4.77 ml) was mixed with diisopropylethylamine (0.162 ml, 0.947 mmol) and O-(benzotriazole-yl)-N,N,N',N'-tetramethyluronium hexafluorophosphate (361.8 mg, 0.954 mmol), and stirred for 30 min at a room temperature. The compound (10) (400 mg, 0.477 mmol) dissolved in methylene chloride (4.8 ml) was added to the resulting solution and stirred for one hour. The resulting mixture was washed with water. An organic layer was collected and dehydrated with anhydrous sodium sulfate, so that the solvent was distilled out under a reduced pressure. The residue was purified with the silica gel chromatography to give the compound (1a) (349 mg, 61%).

$^1$HNMR (DMSO-d$_6$) δ 1.59-1.65(2H, m), 2.15(6H, s), 2.26-2.28(2H, t, J=7.1 Hz), 2.56-2.59(2H, t, J=7.0 Hz), 3.18-3.22(2H, m,), 3.37-3.50(6H, m), 3.81(3H, s 3.83 (3H, s), 3.85 (3H, s), 3.94 (3H, s), 3.97 (3H, s), 3.99(3H, s), 4.27-4.30(4H, m), 4.73(4H, s), 6.88(1H, d, J=1.7 Hz), 6.94(1H, d, J=1.5 Hz), 7.02(1H, s), 7.16(1H, d, J=1.7 Hz), 7.19(1H, d, J=1.5 Hz), 7.26(1H, d, J=1.7 Hz), 7.35-7.36(2H, m), 7.46(1H, s), 7.49 (1H, s), 7.86-7,87(1H, t, J=5.6 Hz), 7.91-7.93(1H, t, J=5.5 Hz), 7.98-7.80(1H, t, J=5.5 Hz), 8.05-8.08(1H, t, J=5.7 Hz), 9.77 (1H, s), 9.88 (1H, s), 10.03(1H, s), 10.06(1H, s), 10.19 (1H, s); $^{13}$CNMR (DMSO-d$_6$) δ 27.2, 35.1, 35.1, 35.3, 36.0, 36.1, 36.2, 36.4, 36.5, 37.4, 38.8, 39.0, 45.3, 57.3, 69.8, 71.7, 71.8, 77.9, 78.0, 79.3, 104.1, 104.8, 106.1, 114.6, 114.9, 118.0, 119.4, 119.6, 121.4, 1221.7, 122.2, 122.3, 122.4, 123.5, 126.6, 127.2, 134.1, 134.4, 136.2, 138.9, 155.9, 156.3, 158.9, 158.9, 159.2, 161.2, 168.2, 168.6, 169.0. MS m/z calcd for $C_{55}H_{66}FeN_{19}O_9^+$: 1192.46403, found 1192.37089.

The compounds (1b) and (1c) were obtained by using the compounds (26b) and (26c), respectively, instead of the compound (26a) as a starting material in accordance with the above general synthesis method. The compound (2) was obtained by using the compounds (26a) and (20) as a starting material in accordance with the above general synthesis method.

1b:
$^1$H NMR (500 MHz, DMSO) δ 1.59-1.63 (2H, m), 1.80-1.83 (2H, m), 2.14 (6H, s), 2.23-2.26 (2H, t, j=6.8 Hz), 2.31-2.34 (2H, t, j=7.2 Hz), 3.18-3.23 (4H, m), 3.44-3.50 (4H, m), 3.80 (3H, s), 3.83 (3H, s), 3.85 (3H, s), 3.94 (3H, s), 3.96 (3H, s), 3.99 (3H, s), 4.29-4.32 (4H, d), 4.74 (4H, s) 6.90 (1H, s), 6.93 (1H, s), 7.04 (1H, s), 7.16 (1H, s), 7.22 (1H, s), 7.28 (1H, s) 7.39 (1H, m), 7.50 (1H, s), 7.53 (1H, s), 7.91-7.93 (1H, t, j=5.0 Hz), 8.04 (1H, t), 8.11-8.12 (1H, t, j=5.1 Hz), 8.14-8.16 (1H, t, j=5.3 Hz), 9.89 (1H, s), 9.98 (1H, s), 10.23 (1H, s), 10.24 (1H, s), 10.38 (1H, s).

1c:
$^1$H NMR (500 MHz, DMSO) δ 1.58-1.63 (2H, m, j=7.1 Hz), 1.72-1.75 (2H, m, j=6.7 Hz), 2.13 (6H, s), 2.22-2.25 (2H, t, j=7.1 Hz), 2.56-2.58 (2H, t, j=7.0 Hz), 3.17-3.21 (2H, q, j=6.1, 6.6 Hz), 3.22-3.26 (2H, q, j=6.1, 6.6 Hz), 3.44-3.48 (2H, q, j=6.1, 6.8 Hz), 3.80 (3H, s), 3.83 (3H, s), 3.85 (3H, s), 3.94 (3H, s), 3.96 (3H, s), 3.99 (3H, s), 4.30-4.32 (4H, m), 4.72-4.75 (4H, m), 6.89 (1H, d, j=2.0 Hz), 6.92 (1H, d, j=1.7 Hz), 7.03 (1H, d, j=1.7 Hz), 7.17 (1H, d, j=1.7 Hz), 7.21 (1H, d, j=1.7 Hz), 7.30 (1H, d, j=1.7 Hz) 7.39 (2H, d, j=2.2 Hz), 7.50 (1H, s), 7.52 (1H, s), 7.93-7.95 (1H, t, j=5.9 Hz), 7.99-8.01 (1H, t, j=5.9 Hz, 8.14-8.16 (1H, t, j=5.9 Hz), 9.97 (1H, s), 9.99 (1H, s), 10.24 (1H, s), 10.27 (1H, s), 10.38 (1H, s).

Compound (2):
$^1$HNMR (DMSO-d$_6$) δ 1.59-1.62(2H, t, J=7.0 Hz), 2.14 (6H, s), 2.23-2.25(2H, t, J=7.0 Hz), 2.55-2.60(4H, m), 3.17-3.21(2H, m), 3.35-3.37(2H, m), 3.42-3.50(6H, m), 3.80(3H.s), 3.83(3H, s), 3.91 (3H, s), 3.93(3H, s), 3.96(3H, s), 4.25-4.26(2H, m), 4.29(2H, m), 4.72-4.73(2H, m), 4.74-4.75 (2H, m), 6.89(1H, d, J=1.8 Hz), 6.93(1H, d, J=1.7 Hz), 6.95 (1H, s), 7.21(1H, d, J=1.7 Hz), 7.31(1H, d, J=1.6 Hz) 7.32 (1H, s) 7.41(1H, s) 7.52(1H, s) 7.99-8.01(2H m) 8.10-8.12

(2H, m) 8.34(1H, t, J=6.0 Hz) 9.95(1H, s) 10.0(1H s) 10.2 (1H, s) 10.2(1H, s) 10.3(1H, s).

Example 4

Synthesis of Fc-PIA 3 (Compound 3)

The compound (29) (300 mg, 0.293 mmol) was dissolved in 20% trifluoro acetic acid/methylenechloride (1.16 ml, 2.93 mmol) and stirred for one hour at a room temperature. The solution was washed with water. An organic layer was collected and dehydrated with anhydrous sodium sulfate, so that the solvent was distilled out under a reduced pressure. The residue was dissolved inmethylene chloride (2.9 ml), mixed with diisopropylamine (0.10 ml, 0.586 mmol), ferrocene carboxylic acid (67.4 mg, 0.293 mmol) and O-(benzotriazole-yl)-N,N,N',N'-tetramethyluronium hexafluorophosphate (111.1 mg, 0.293 mmol), and stirred for 10 hours at a room temperature. The resulting mixture was washed with water. An organic layer was collected and dehydrated with anhydrous sodium sulfate, so that the solvent was distilled out under a reduced pressure. The residue was purified with silica gel chromatography to give the compound (3) (204 mg, 61%).

$^1$HNMR (DMSO-$d_6$) δ 1.57-1.62(2H, m), 2.12(6H, s), 2.22-2.24(2H, t, J=7.0 Hz), 3.16-3.20(2H, m), 3.37-3.43(2H, m), 3.80(3H, s), 3.83(3H, s), 3.85(3H, s), 3.93(3H, s), 3.96(3H, s), 3.98(3H, s), 4.22(5H, s), 4.36-4.37 (2H, m), 4.85 (2H, m), 4.94 (2H, m), 6.86 (1H, d, J=1.7 Hz), 6.99(1H, d, J=1.7 Hz), 7.02(1H, d, J=1.0 Hz), 7.17 (1H, d, J=1.7 Hz), 7.20 (1H, d, J=1.7 Hz), 7.28 (1H, d, J=1.7 Hz), 7.37 (1H, s), 7.38 (1H, d, J=1.7 Hz), 7.49(1H, s), 7.52(1H, s), 7.86-7.87(1H, d, J=1.7 Hz), 8.05-8.10(2H, m), 9.95(1H, s), 10.04(1H, s), 10.24(1H, s), 10.25(1H, s), 10.27(1H, s), 10.36(1H, s); $^{13}$CNMR (DMSO-$d_6$) δ 27.2, 35.1, 35.1, 35.3, 36.0, 36.1, 36.2, 36.4, 36.5, 37.4, 38.8, 39.0, 45.3, 57.3, 69.8, 71.7, 71.8, 77.9, 78.0, 79.4, 104.1, 104.8, 106.1, 114.6, 114.9, 118.0, 119.4, 119.6, 121.4, 121.7, 122.0, 122.3, 122.4, 123.5, 126.6, 127.2, 134.1, 134.4, 136.2, 138.9, 155.9, 156.3, 158.9, 158.9, 159.2, 161.2, 168.2, 168.6, 169.0. MS m/z calcd for $C_{53}H_{63}FeN_{18}O_8^+$: 1135.44257, found 1135.43889.

Example 5

Properties of the Compounds 1a, 2 and 3 as Ligand

Figure 2:
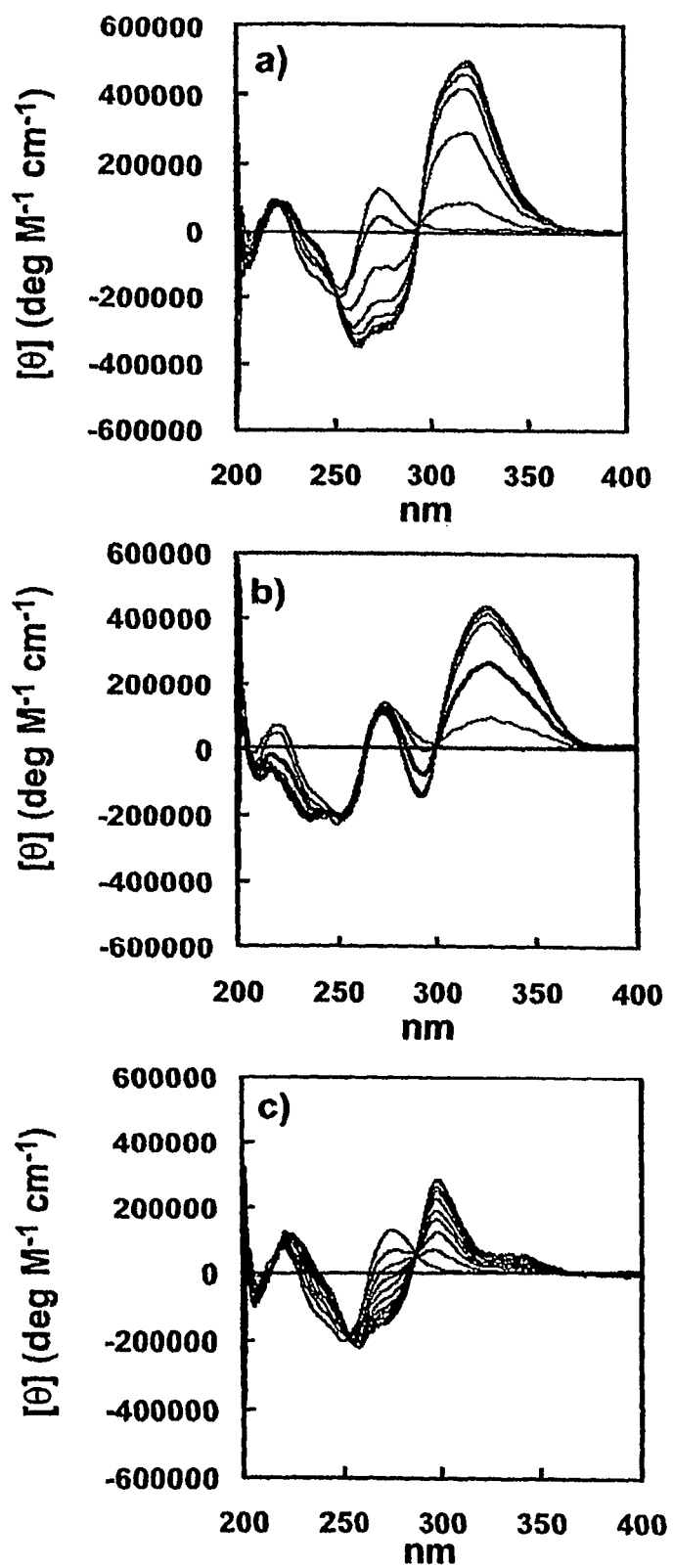
FIG. 2 shows CD profile in the titration of the 11-mer DNA prepared in Example 5. The titration of the double-stranded DNA (5 μM) with the compound (1a) (0–1.8 equivalent)(a), with the compound (3) (0-1.6 equivalent)(b), and with the compound (2) (0-2.0 equivalent)(c), respectively.

Similarly with Example 2, the binding of the above compounds to the target DNA (5'GACTGCGTAGG3'/3'CTGA CGCATCC5') was detected with CD spectrum in order to confirm its utility as a ligand for the double-stranded helical DNA. The results are in FIG. 2. It is well known that elliptical polarization at 300-360 nm was induced by the interaction with a minor groove (Pilch, D. S.; Poklar, N.; Baird, E. E.; Dervan, P. B.; Breslauer, K. J. Biochemistry, 2002, 38, 2143-2151). As a result, the addition of the solution of target DNA (5.0 μM) caused concentration-dependent increase of a positive cotton effect.

Example 6

Detection of the Electrochemical Properties by Cyclic Voltammetry (CV)

Figure 3:
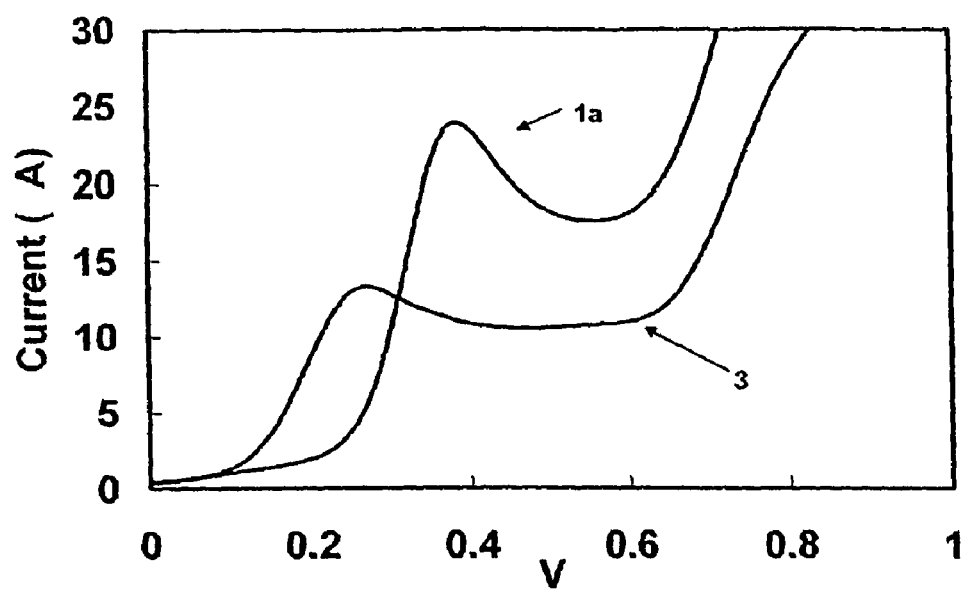
FIG. 3 shows the electrochemical properties of the present compounds, which were obtained in an experiment with a cyclic voltammetry (CV) in Example 6. The experiment was carried out by using the compound of the present invention (5 mM) in N,N-dimethylformamide containing 0.2 M $NaClO_4$. Reference electrode: $AgCl_2$; Counter electrode: Pt; operating Electrode: Pt.

The results of the experiment about the electrochemical properties of the present compounds (1a) and (3) with a cyclic voltammetry (CV) are shownin FIG. 3. They indicate that the compounds according to the present invention have the activities for the electrochemical reaction.

INDUSTRIAL APPLICABILITY

The preset invention may be utilized in various kinds of industrial fields such as, for example, development of drugs, clinical inspection (test), screening of pharmaceuticals, safety test of compounds, food evaluation, medical inspection, medicolegal inspection, brewing, agriculture, forestry, fishery, and livestock farming.

What is claimed is:

1. A ferrocene compound represented by the following formula (I):

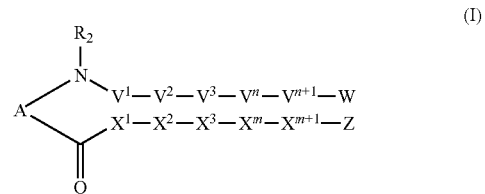

wherein A represents a divalent ferrocene-containing linker represented by the following formula (VI):

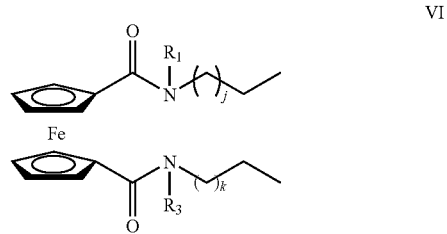

wherein $R_1$ and $R_3$ represent a hydrogen atom or alkyl; j and k represent the same or different integer of from 0 to 5, $R_2$ represents a hydrogen atom or alkyl; n and m represent natural numbers; and wherein each of $V^2$ to $V^{n+1}$ and each of $X^2$ to $X^{m+1}$ is independently represented by the following formula (II) or (II-1):

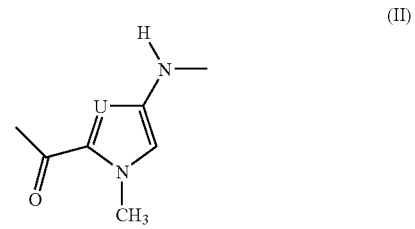

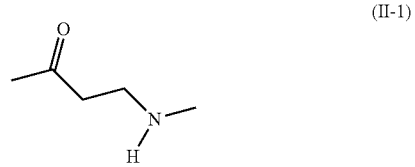

wherein each of $V^1$ and $X^1$ is represented by the formula (II),

W represents the following formula (III):

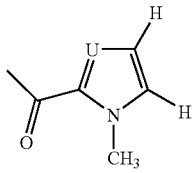

wherein U in the formulae (II) and (III) represents a nitrogen atom, methine or hydroxymethine;
and Z represents the following formulae (IV) or (V):

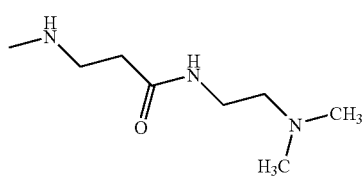

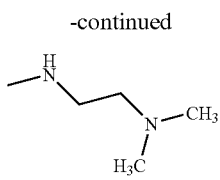

and both ends of each of $V'''$ and $X'''$ in the formula (I) form a (—CO—NH—) bond except that a bond on the side of the ferrocene-containing linker of $V^1$ is (—CO—$NR_2$—).

2. The ferrocene compound according to claim 1 wherein n and m are natural numbers in the range of 3-20.

3. The ferrocene compound according to claim 1 or 2 wherein the number of n is smaller by one than that of m.

4. The ferrocene compound according to claim 1 wherein j and k are 1.

5. The ferrocene compound according to claim 1 wherein $R_1$ and $R_3$ represent a hydrogen atom.

6. The ferrocene compound according to claim 1 wherein $R_1$, $R_2$ and $R_3$ represent alkyl having one or several carbon atoms.

7. The ferrocene compound represented by the following formula (VIII):

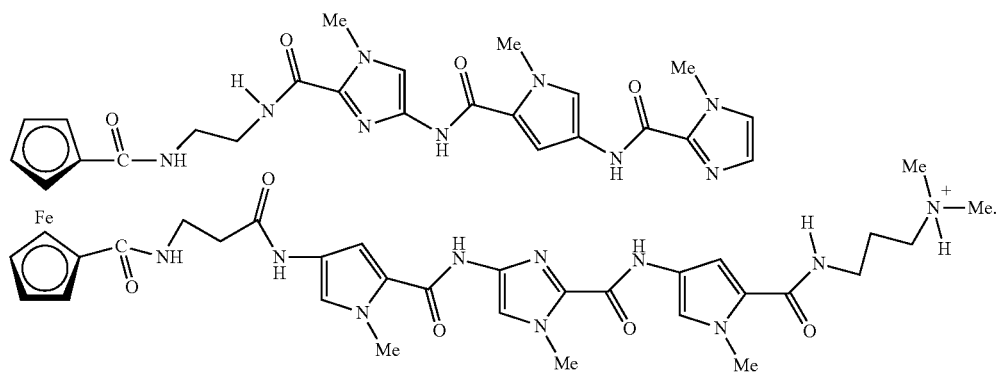

8. The ferrocene compound represented by the following formula (1b):

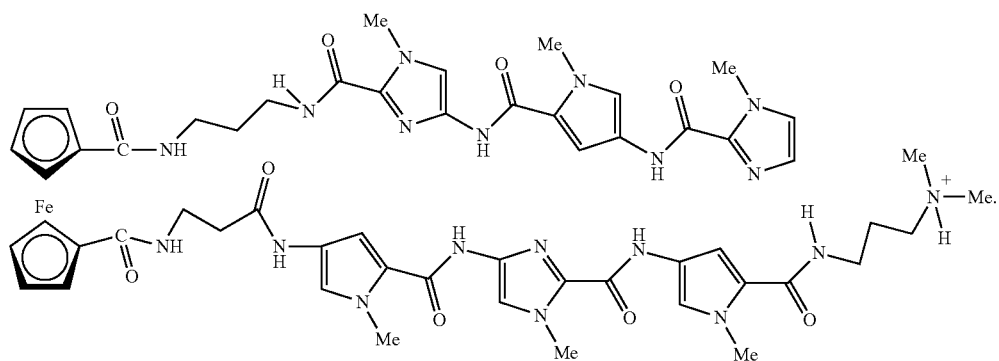

9. The fenocene compound represented by the following formula (1c):
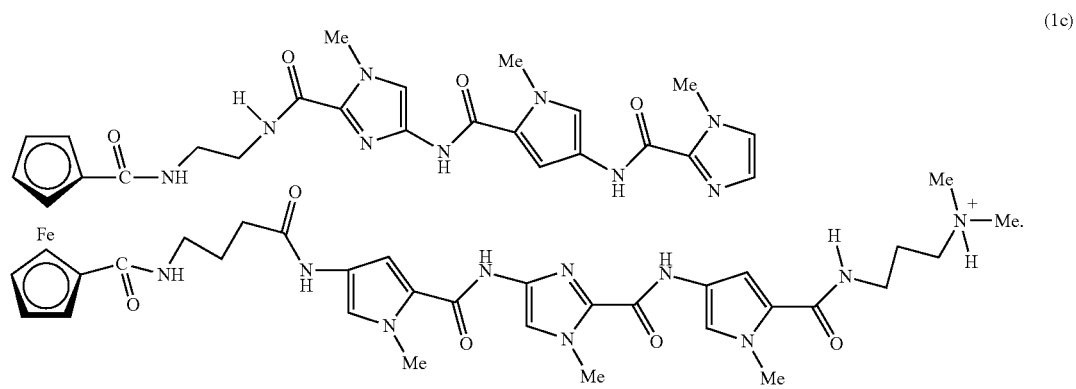
10. The ferrocene compound represented by the following formula (2):
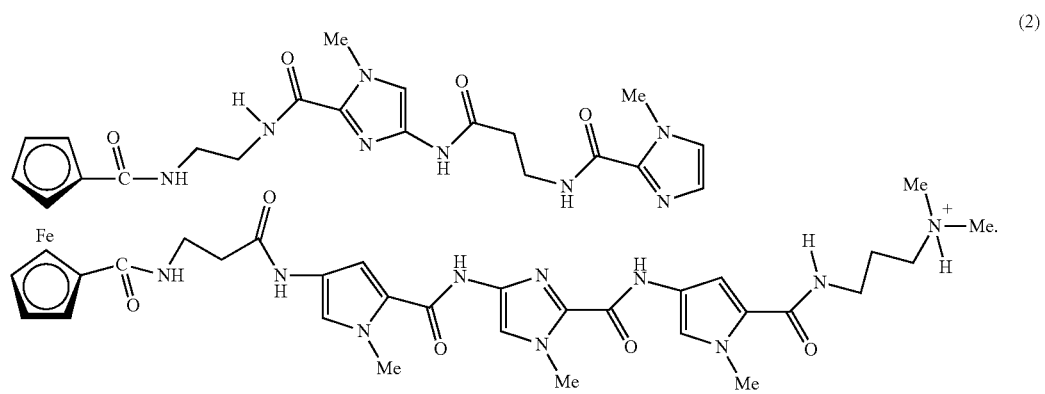
11. A ligand consisting of the ferrocene compound according to claim 1 for sequence-specific detection of double-stranded nucleic acid molecules.
12. The ferrocene compound according to claim 1 wherein $R_1$, $R_2$ and $R_3$ represent hydrogen.
* * * * *